(12) United States Patent
Bandyopadhyay et al.

(10) Patent No.: US 10,661,390 B2
(45) Date of Patent: May 26, 2020

(54) BONE REPLACEMENT MATERIALS

(71) Applicant: Washington State University, Pullman, WA (US)

(72) Inventors: Amit Bandyopadhyay, Pullman, WA (US); Susmita Bose, Pullman, WA (US)

(73) Assignee: Washington State University, Pullman, WA (US)

( * ) Notice: Subject to any disclaimer, the term of this patent is extended or adjusted under 35 U.S.C. 154(b) by 1072 days.

(21) Appl. No.: 15/017,925

(22) Filed: Feb. 8, 2016

(65) Prior Publication Data
US 2016/0228992 A1 Aug. 11, 2016

Related U.S. Application Data

(62) Division of application No. 11/675,006, filed on Feb. 14, 2007, now Pat. No. 9,327,056.
(Continued)

(51) Int. Cl.
*B22F 3/105* (2006.01)
*B22F 3/11* (2006.01)
(Continued)

(52) U.S. Cl.
CPC .............. *B23K 26/342* (2015.10); *A61F 2/28* (2013.01); *A61F 2/30942* (2013.01); *A61F 2/36* (2013.01);
(Continued)

(58) Field of Classification Search
CPC ........ B22F 3/1055; B22F 3/11; B22F 3/1103; B22F 3/1109; B22F 3/1112; B22F 3/1115;
(Continued)

(56) References Cited

U.S. PATENT DOCUMENTS 4,718,914 A 1/1988 Frey
5,026,591 A 6/1991 Henn et al.
(Continued)

FOREIGN PATENT DOCUMENTS

EP 1440669 2/2003
EP 1449544 8/2004
(Continued)

OTHER PUBLICATIONS

W. Meiners, C. Over, K. Wissenbach, R. Poprawe, "Direct Generation of Metal Parts and Tools by Selective Laser Powder Remelting (SLPR)," Solid Freeform Fabrication Symposium, Proceedings from Aug. 9-11, 1999, pp. 655-661. (Year: 1999).*
(Continued)

*Primary Examiner* — Vanessa T. Luk
(74) *Attorney, Agent, or Firm* — Liang IP, PLLC

(57) ABSTRACT

Particular aspects provide novel devices for bone tissue engineering, comprising a metal or metal-based composite member/material comprising an interior macroporous structure in which porosity may vary from 0-90% (v), the member comprising a surface region having a surface pore size, porosity, and composition designed to encourage cell growth and adhesion thereon, to provide a device suitable for bone tissue engineering in a recipient subject. In certain aspects, the device further comprises a gradient of pore size, porosity, and material composition extending from the surface region throughout the interior of the device, wherein the gradient transition is continuous, discontinuous or seamless and the growth of cells extending from the surface region inward is promoted.

20 Claims, 20 Drawing Sheets

Related U.S. Application Data

(60) Provisional application No. 60/773,079, filed on Feb. 14, 2006.

(51) Int. Cl.

| | | |
|---|---|---|
| *A61F 2/28* | (2006.01) | |
| *B23K 26/342* | (2014.01) | |
| *A61F 2/30* | (2006.01) | |
| *A61F 2/36* | (2006.01) | |
| *A61L 27/42* | (2006.01) | |
| *A61L 27/56* | (2006.01) | |
| *B23K 26/70* | (2014.01) | |
| *A61L 27/06* | (2006.01) | |
| *A61L 27/54* | (2006.01) | |
| *B23K 26/00* | (2014.01) | |
| *B23K 103/14* | (2006.01) | |
| *B23K 103/16* | (2006.01) | |
| *B33Y 10/00* | (2015.01) | |
| *B33Y 50/00* | (2015.01) | |
| *B33Y 70/00* | (2020.01) | |
| *B33Y 80/00* | (2015.01) | |

(52) U.S. Cl.
CPC .............. *A61L 27/06* (2013.01); *A61L 27/42* (2013.01); *A61L 27/427* (2013.01); *A61L 27/54* (2013.01); *A61L 27/56* (2013.01); *B22F 3/105* (2013.01); *B22F 3/1055* (2013.01); *B22F 3/1109* (2013.01); *B22F 3/1146* (2013.01); *B23K 26/0006* (2013.01); *B23K 26/70* (2015.10); *A61F 2/3094* (2013.01); *A61F 2/367* (2013.01); *A61F 2/3676* (2013.01); *A61F 2002/2817* (2013.01); *A61F 2002/30004* (2013.01); *A61F 2002/30006* (2013.01); *A61F 2002/30011* (2013.01); *A61F 2002/30028* (2013.01); *A61F 2002/3093* (2013.01); *A61F 2002/3097* (2013.01); *A61F 2002/30115* (2013.01); *A61F 2002/30118* (2013.01); *A61F 2002/30179* (2013.01); *A61F 2002/30224* (2013.01); *A61F 2002/30235* (2013.01); *A61F 2002/30322* (2013.01); *A61F 2002/30593* (2013.01); *A61F 2002/30616* (2013.01); *A61F 2002/30677* (2013.01); *A61F 2002/30838* (2013.01); *A61F 2002/30909* (2013.01); *A61F 2230/0006* (2013.01); *A61F 2230/0058* (2013.01); *A61F 2230/0069* (2013.01); *A61F 2250/0014* (2013.01); *A61F 2250/0023* (2013.01); *A61F 2250/0026* (2013.01); *A61F 2310/00017* (2013.01); *A61F 2310/00023* (2013.01); *A61F 2310/00029* (2013.01); *A61F 2310/00047* (2013.01); *A61F 2310/00053* (2013.01); *A61F 2310/00113* (2013.01); *A61F 2310/00155* (2013.01); *A61F 2310/00179* (2013.01); *A61F 2310/00185* (2013.01); *A61F 2310/00227* (2013.01); *A61F 2310/00293* (2013.01); *A61L 2300/404* (2013.01); *A61L 2300/406* (2013.01); *A61L 2300/414* (2013.01); *A61L 2430/02* (2013.01); *B22F 2998/00* (2013.01); *B23K 2103/14* (2018.08); *B23K 2103/16* (2018.08); *B33Y 10/00* (2014.12); *B33Y 50/00* (2014.12); *B33Y 70/00* (2014.12); *B33Y 80/00* (2014.12)

(58) Field of Classification Search
CPC .............. B22F 3/1118; B22F 3/1146; B22F 2003/1056; B22F 2003/1057; B22F 2003/1058; B22F 2003/1059; B22F 2003/1106; B22F 2207/17; B22F 7/002; B22F 7/004; B22F 7/006; B22F 3/105; B22F 2003/1052
See application file for complete search history.

(56) References Cited

U.S. PATENT DOCUMENTS

| | | | |
|---|---|---|---|
| 5,032,552 A | 7/1991 | Nonami et al. | |
| 5,246,530 A | 9/1993 | Bugle et al. | |
| 5,338,772 A | 8/1994 | Bauer et al. | |
| 5,484,286 A | 1/1996 | Hansson | |
| 5,843,172 A * | 12/1998 | Yan | A61F 2/82 623/1.42 |
| 6,013,591 A | 1/2000 | Ying | |
| 6,046,426 A * | 4/2000 | Jeantette | B01F 13/0255 219/121.63 |
| 6,261,493 B1 * | 7/2001 | Gaylo | B29C 33/3814 264/86 |
| 6,471,993 B1 | 10/2002 | Shastri et al. | |
| 6,689,170 B1 | 2/2004 | Larsson et al. | |
| 6,790,233 B2 | 9/2004 | Brodke et al. | |
| 7,048,541 B2 | 5/2006 | Hall et al. | |
| 2002/0062154 A1 | 5/2002 | Ayers | |
| 2002/0173850 A1 | 11/2002 | Brodke et al. | |
| 2003/0114936 A1 * | 6/2003 | Sherwood | A61F 2/28 623/23.58 |
| 2003/0157460 A1 * | 8/2003 | Hall | A61C 8/0012 433/174 |
| 2003/0193106 A1 | 10/2003 | Yu et al. | |
| 2004/0019385 A1 | 1/2004 | Ayers et al. | |
| 2004/0023784 A1 | 2/2004 | Yu et al. | |
| 2004/0082999 A1 | 4/2004 | Mathys, Jr. et al. | |
| 2004/0101822 A1 | 5/2004 | Wiesner et al. | |
| 2004/0142013 A1 | 7/2004 | Rubsamen | |
| 2004/0191106 A1 * | 9/2004 | O'Neill | A61F 2/30907 419/2 |
| 2004/0243237 A1 | 12/2004 | Unwin et al. | |
| 2004/0254668 A1 | 12/2004 | Jang et al. | |
| 2005/0123672 A1 * | 6/2005 | Justin | A61C 8/0012 427/2.26 |
| 2005/0221072 A1 | 10/2005 | Dubrow et al. | |
| 2006/0078590 A1 | 4/2006 | Hermansson et al. | |
| 2006/0188542 A1 | 8/2006 | Bobyn et al. | |
| 2006/0229715 A1 | 10/2006 | Istephanous et al. | |
| 2007/0098811 A1 | 5/2007 | Lu et al. | |
| 2007/0203584 A1 | 8/2007 | Bandyopadhyay et al. | |
| 2009/0276056 A1 | 11/2009 | Bose | |

FOREIGN PATENT DOCUMENTS

| | | |
|---|---|---|
| WO | W09511639 | 5/1995 |
| WO | WO 99/66966 | 12/1999 |
| WO | WO20000072777 | 12/2000 |
| WO | WO2004008984 | 1/2004 |
| WO | WO2005000159 | 1/2005 |
| WO | WO2006116752 | 11/2006 |
| WO | WO2007124511 | 11/2007 |

OTHER PUBLICATIONS

Office Action in U.S. Appl. No. 14/682,343 dated Aug. 25, 2016, 19 pages.
Notice of Allowance in U.S. Appl. No. 12/211,005 dated Aug. 12, 2014, 25 pages.
Notice of Allowance in U.S. Appl. No. 12/298,012 dated Jan. 14, 2015, 12 pages.
Office Action in U.S. Appl. No. 14/682,343 dated Nov. 13, 2015, 16 pages.
Anderson, J.M. et al. "Biodegradation and biocompatibility of PLA and PLGA microspheres," Advanced Drug Delivery Reviews 28 (1997) 5-24.
Andreadis, S.T. et al. "Biomimetric approaches to protein and gene delivery for tissue regeneration," Trends in Biotechnology 24 (2006) 331-337.

(56) References Cited

OTHER PUBLICATIONS

Angell, F. et al. "Influence of glass composition and alteration solution on leached silicate glass structure: A solid-state NMR investigation," Geochimica et Cosmochimica Acta 70 (2006) 2577-2590.
Balas F. et al., "L-Trp adsorption into silica mesoporous materials to promote bone formation," Acta Biomaterialia 4 (2008) 514-522.
Baldwin, S.P. et al. "Materials for protein delivery in tissue engineering," Advanced Drug Delivery Reviews 33 (1998) 71-86.
Barbe, C. et al. "Silica Particles: A Novel Drug-Delivery System," Adv. Mater. 16 (2004) 1959-1966.
Blom, E.J. et al. "Transforming growth factor-131 incorporation in an a-tricalcium phosphate/dicalcium phosphate dihydrate/tetracalcium phosphate monoxide cement: release characteristics and physiochemical properties," Biomaterials 23 (2002) 1261-1268.
Casey, W.H. et al. "Leaching and reconstruction at the surfaces of dissolving chainsilicate minerals," Nature 366 (1993) 253-256.
Chen, J.J. et al. "Solubility and structure of calcium silicate hydrate," Cement and Concrete Research 34 (2004) 1499-1519.
De Aza, P.N. et al. "Bioactivity of Wollastonite Ceramics: In Vitro Evaluation," Scripta Metallurgica et Materialia 31 (1994) 1001-1005.
De Aza, P.N. et al. "Morphological and structural study of pseudowallastonite implants in bone," Journal of Microscopy 197 (2000) 60-67.
Ginebra, M.-P. et al. "Calcium phosphate cements: Competitive drug carriers for the musculoskeletal system?," Biomaterials 27 (2006) 2171-2177.
Haesslein, A. et al. "Effect of macromer molecular weight on in vitro ophthalmic drug release from photo-crosslinked matrices," Acta Biomaterialia 4 (2008) 1-10.
Hartmann, M. "Ordered Mesoporous Materials for Bioadsorption and Biocatalysis," Chem. Mater. 17 (2005) 4577-4593.
Hartmann, M. et al. "Adsorption of Vitamin Eon Mesoporous Carbon Molecular Sieves," Chem. Mater. 17 (2005) 829-833.
Hench, L.L. "Bioceramics: From Concept to Clinic," J. Am. Ceram. Sci. 74 (1991) 1487-1510.
Holland, T.A. et al. "Advances in drug delivery for articular cartilage," Journal of Controlled Release 86 (2003) 1-14.
Horcajada, P. et al. "Bioactivity in ordered mesoporous materials," Solid State Sciences 6 (2004) 1295-1300.
Kokubo, T. "Novel bioactive materials with different mechanical properties," Biomaterials 24 (2003) 2161-2175.
Kumta, P.N. et al. "Nanostructured calcium phosphates for biomedical applications: novel synthesis and characterization," Acta Biomaterialia 1 (2005) 65-83.
Lee, J.Y. et al. "Transforming Growth Factor (TGF)-131 Releasing Tricalcium Phosphate/Chitosan Microgranules as Bone Substitutes," Pharmaceutical Research 21 (2004) 1790-1796.
Li, P. et al. "The Electrochemistry of a Glass Surface and its Application to Bioactive Glass in Solution," Journal of Non-Crystalline Solids 119 (1990) 112-118.
Lin, K. et al. "Study of the mechanical property and in vitro biocompatibility of CaSi03 ceramics," Ceramics International 31 (2005) 323-326.
Liong, M. et al. "Multifunctional Inorganic Nanoparticles for Imaging, Targeting, and Drug Delivery," ACS Nano 2 (2008) 889-896.
Liu, X. et al. "Apatite formed on the surface of plasma-sprayed wollastonite coating immersed in simulated body fluid," Biomaterials 22 (2001) 2007-2012.
Luginbuehl, V. et al. "Localized delivery of growth factors for bone repair," European Journal of Pharmaceutics and Biopharmaceutics 58 (2004) 197-208.
Melillo, M. et al. "Structural Characteristics of Activated Carbons and Ibuprofen Adsorption Affected by Bovine Serum Albumin," Langmuir 20 (2004) 2837-2851.
Olton, D. et al. "Nanostructured calcium phosphates (NanoCaPs) for non-viral gene delivery: Influence of the synthesis parameters on transfection efficiency," Biomaterials 28 (2007) 1267-1279.
Panyam, J. et al. "Biodegradable nanoparticles for drug and gene delivery to cells and tissue," Advanced Drug Delivery Reviews 55 (2003) 329-347.
Panda, S.K. et al. "Adsorption of organic molecules on silica surface," Advances in Colloid and Interface Science 121 (2006) 77-110.
Rai, B. et al. "Novel PCL-based honeycomb scaffolds as drug delivery systems for rhBMP-2," Biomaterials 26 (2005) 3739-3748.
Sahai, N. et al. "Molecular Orbital Study of Apatite (Ca5(P04)pH) Nucleation at Silica Bioceramic Surfaces," J. Phys. Chem. B 104 (2000) 4322-4341.
Schmidt, H.T. et al. "Assembly of Aqueous-Cored Calcium Phosphate Nanoparticles for Drug Delivery," Chem. Mater. 2004, 16, 4942-4947.
Schmidt, S.M. et al. "Surfactant based assembly of mesoporous patterned calcium phosphate micron-sized rods," Microporous and Mesoporous Materials 94 (2006) 330-338.
Seeherman, H. et al. "Delivery of bone morphogenetic proteins for orthopedic tissue regeneration," Cytokine & Growth Factor Reviews 16 (2005) 329-345.
Slowing, 1.1. et al. "Mesoporous Silica Nanoparticles for Drug Delivery and Biosensing Applications," Adv. Funct. Mater. 17 (2007) 1225-1236.
Vallet-Regi, M. et al. "A New Property of MCM-41: Drug Delivery System," Chem. Mater. 13 (2001) 308-311.
Wan, X. et al. "Preparation and in vitro bioactivities of calcium silicate nanophase materials," Materials Science and Engineering C 25 (2005) 455-461.
Weissbart, E.J. et al. "Wallastonite: Incongruent dissolution and leached layer formation," Geochimica et Cosmochimica Acta 64 (2000) 4007-4016.
Xia, W. et al. "Well-ordered mesoporous bioactive glasses (MBG): A promising bioactive drug delivery system," Journal of Controlled Release 110 (2006) 522-530.
Xu, Z.P. et al. "Inorganic nanoparticles as carriers for efficient cellular delivery," Chemical Engineering Science 61 (2006) 1027-1040.
Xue, W. et al. "In vivo evaluation of plasma-sprayed wollastonite coating," Biomaterials 26 (2005) 3455-3460.
Saravanapavan, Journal of Non-Crystalline Solids, 318, pp. 1-13, 2003.
Saravanapavan, Journal of Non-Crysatlline Solids, 318, pp. 14-26, 2003.
Office Action in U.S. Appl. No. 12/211,005 dated Jul. 9, 2010, 11 pages.
Office Action in U.S. Appl. No. 12/211,005 dated Mar. 23, 2011, 14 pages.
Office Action in U.S. Appl. No. 12/211,005 dated Apr. 10, 2014, 9 pages.
Bandyopadhyay, et al., "Calcium Phosphate-Based Resorbable Ceramics: Influence of MgO, ZnO, and Si02 Dopants," J. Am. Ceram. Soc., 89 [9], pp. 2675-2688 (2006).
Bandyopadhyay, et al., "Influence of ZnO doping in calcium phosphate ceramics", in press, Materials Science and Engineering C, Nov. 2005.
Bertoni, et al., "Nanocrystals of Magnesium and fluoride substituted hydroxyapatite". J. Inorg. Biochem., 72, 29-35 (1998).
Office Action in U.S. Appl. No. 12/298,012 dated Aug. 18, 2014, 15 pages.
Borden et al. The sintered microsphere matrix for bone tissue engineering: In vitro osteoconductivity studies. 2002. Wiley Periodicals, Inc. pp. 421-429.
Gomes et al. Biodegradable polymers and composites in biomedical applications: from catgut to tissue engineering. 2004. Maney for the Institute and ASM International. vol. 49. No. 5. pp. 261-273.
Office Action in U.S. Appl. No. 14/538,418 dated Apr. 4, 2016, 10 pages.
Office Action in U.S. Appl. No. 14/682,343 dated May 5, 2016, 16 pages.
Camire et al. Material characterization and in vivo behavior of silicon substituted alpha-tricalcium phosphate cement. Sep. 23, 2005. J Biomed Mater Res B Appl Biomater. <htto://dx.doi.org/1 0.1 002/jbm.b.30385>.

(56) References Cited

OTHER PUBLICATIONS

Bose, et al., "Synthesis and characterization of hydroxyapatite nanopowders by emulsion technique," Chern Mater., 15 (23), 4464-4469 (2003).

Bose, et al., "Synthesis of hydroxyapatite nanopowders via sucrose-templated sol-gel method," Journal of the American Ceramic Society, 86 [6], pp. 1055-1057 (2003).

Bose, et al., "Pore Size and Pore Volume Effects on Alumina and TCP Ceramic Scaffolds," Materials Science and Engineering C, 23, pp. 479-486 (2003).

Burg, et al., "Biomaterial developments for bone tissue engineering". Biomaterials, 21 [23]2347-59 (2000).

Buser, et al., "Localized ridge augmentation using guided bone regeneration"; pp. 189-233 in Guided bone regeneration in implant dentistry, Edited by D. Buser, C. Dahlin and R. K. Schenk, Quintessenz, Chicago, 1994.

De Groot, "Effect of porosity and physicochemical properties on the stability, resorption, and strength of calcium phosphate ceramics". In Bioceramics: Material characteristics versus in-vivo behavior, Ann. N.Y. Acad. Sci., 523,227 (1998).

Doi, et al., "Development of a new calcium phosphate cement that contains sodium calcium phosphate," Biomaterials 22 (2001) 847-845.

Ducheyne, et al., "Bioactive ceramics: the effect of surface reactivity on bone formation and bone cell function," Biomaterials (1999) 20:23-24, pp. 2287-2303.

Fujimura, et al., "A bioactive bone cement containing Bis-GMA resin and A-W glass-ceramic as an augmentation graft material on mandibular bone," Clin Ora/Implants Res (2003) 14, pp. 659-667.

Hashizume, et al., "Stimulatory effect of 133-alanyl-1-histidinato zinc on cell proliferation is dependent on protein synthesis in osteoblastic MC3T3-E1 cells", Mol. Cell Biochem., 122, 59-64 (1993).

Hattiangadi, et al., "Strength Degradation of Nonrandom Porous Ceramics Under Uniaxial Compressive Loading," Journal of the American Ceramic Society, 83 [11], pp. 2730-2736 (2000).

Hayakawa, et al., "Mechanism of apatite formation on a sodium glass in a simulated body fluid", J. Am. Ceram. Soc., 82 f812155-60 (1999).

Hulbert, et al. Potential of ceramic materials as permanently implantable skeletal prosthesis. J Biomed Mater Res 1970; 4:443.

Inoue, et al., "In vivo effect of fluoride-substituted apatite on rat bone," Dent Mater J. Sep. 2005; 24 (3); 398.

Ito, et al., "Preparation, solubility, and cytocompatibility of zinc-releasing calcium phosphate ceramics", J. Biomed. Mater. Res., 50 [2]178-183 (2000).

Josch E K, et al., Chemical and physicochemical characterization of porous hydroxyapatite ceramics made of natural bone. Biomaterals. 21:1645-1658 (2000).

Kalita, et al., "Development of controlled porosity polymer-ceramic composite scaffolds via fused deposition modeling," Materials Science and Engineering C 23:611-620 (2003).

Kalita, et al., "Effects of Mg0—Ca0—P20 5—Na20 based additives on mechanical and biological properties of hydroxyapatite," in press, Journal of Biomedical Materials Research, Jun. 2004, pp. 35-44.

Kalita, et al., "CaO—P20s—Na20 based sintering additives for hydroxyapatite (HAp) ceramics," Biomaterials, 25:12, pp. 2331-2339 (2004).

Kamakura, et al., Implanted octacalcium phosphate is more resorbable than 13-tricalcium phosphate and hydroxyapatite. J Biomed Mater Res. 59:29-34 (2002).

Kim, et al., "Synthesis of Si, Mg substituted hydroxyapatites and their sintering behaviors", Biomaterials. 24 f81 1389-98 (2003).

Kishi, et al., "Inhibitory effect of zinc compounds on osteoclast-like cell formation in mouse marrow culture", Biochem. Pharmacal., 48, 1225-1230 (1994).

Knabe, et al., Effect of rapidly resorbable calcium phosphates and a calcium phosphate bone cement on the expression of bone-related genes and proteins in vitro, J Biomed Mater Res. 69A: 145-154 15 (2004).

Knabe, et al., "The functional expression of human bone-derived cells grown on rapidly resorbable calcium phosphate ceramics", Biomaterials. 25 [2] 335-44 (2004).

Knowles, et al., "Sintering effects in a glass reinforced hydroxyapatite", Biomaterials, 17 [14] 1437 (1996).

Kokubo, et al., "Solutions able to reproduce in vivo surface-structure changes in bioactive glassceramicA-W3", J. Biomed. Mater. Res., 24,721-34 (1990).

Lansdown, Silver 2: toxicity in mammals and how its products aid wound repair 11, 173 (2002).

Larrabee, et al., A ferric calcium phosphorous oxide (FE CAP) ceramic for rebuilding bone. Biomed Sci Instrum. 29:59-64 (1993).

Leng, et al., "Identifying Calcium Phosphates Formed in Simulated Body Fluid by Electron Diffraction", Hey. Eng. Mater., 254 [25]339-42 (2004).

Manjubala, et al., Effect of Ti02Ag20 additives on the formation of calcium phosphate based functionally graded bioceramics. Biomaterials. 21:1995-2002 (2000).

Marcacci, et al., "Reconstruction of extensive long-bone defects in sheep using porous hydroxyapatite sponges," Calcif Tissue Int (1999) 64, pp. 83-90.

Moonga, et al., "Zinc is a potent inhibitor of osteoclastic bone resorption in vitro", J. Bone Miner. Res., 10 [3]453-457 (1995).

Moritz, et al., "Local induction of calcium phosphate formation on Ti02 coatings on titanium via surface treatment with a C02 laser," J of biomed mater res A, 65 (2003) 9-16.

Otsuka, et al., Effect of controlled zinc release on bone mineral density from injectable Zncontaining 13-tricalcium phosphate suspension in zinc-deficient diseased rats. J Biomed Mater Res. 69A:552-560 (2004).

Percival, "Bone health & Osteoporosis", Appl. Nutr. Sci. Rep., 5 [4]1 (1999).

Qiu, et al., "Effect of strontium ions on the growth of ROS17 /2.8 cells on porous calcium polyphosphate scaffolds", Biomaterials; 27 f811277-86 (2006).

Ramires, et al., "The influence of titania/hydroxyapatite composite coatings on in vitro osteoblasts behaviour," Biomaterials, 22(12):1467-74 (2001).

Rodriguez-Lorenzo, et al., "Influence of fluorine in the synthesis of apatites, synthesis of solid solutions of hydroxyl-fluorapatite," Biomaterials 24 (2003) 3777-3785.

Rokusek, et al., "Interaction of human osteoblasts with bioinert and bioactive ceramic substrates", J. Biomed. Mater. Res., 75A f31588-94 (2005).

Seeley, et al., "Tricalcium phosphate based resorbable ceramics: Influence of NaF and GaO addition," Mater. Sci. Enq. C, vol. 28, Issue 1, pp. 11-17 (2008).

Seeley, et al., "Influence of Ti02 and Ag 20 Addition on Tricalcium Phosphate Ceramics", J. Biomed. Mater. Res., vol. 82A, Issue 1, pp. 113-121, Jul. 2007.

Suchanek, et al., "Processing and Properties of Hydroxyapatite-Based Biomaterials for Use as Hard Tissue Replacement Implants", J. Mater. Res., 13 [1]94-109 (1998).

Tadjoedin, et al., "High concentrations of bioactive glass material (BioGran®) vs. autogenous bone for sinus floor elevation," Clinical Ora/Implants Research (2002) 13:4, pp. 428-436.

Wang, "Ca/P ratio effects on the degradation of hydroxyapatite in vitro," J. of Biomedical Materials Research part A, 67A:2, pp. 599-608, publication year: 2003.

Yaszemski, et al., "Evolution of bone transplantation: molecular, cellular and tissue strategies to engineer human bone," Biomaterials (1996) 17:2, pp. 175-185.

Yin, et al., "Density Functional Study of Structural, Electronic and Vibrational properties of Mg-and Zn-doped Tricalcium Phosphate Biomaterials", Biomaterials 23 f201 4155-4163 (2002).

Zamir, et al., "Molecular complexity and dynamics of cell-matrix adhesions", J. Cell Sci. 114 [20] 3583-90 (2001).

(56) References Cited

OTHER PUBLICATIONS

Zerbo, et al., "Histomorphometry of human sinus floor augmentation using a porous 13-tricalcium phosphate: a prospective study," Clinical ora/Implant Research (2004) 15, pp. 724-732.

Zerbo, et al., Histology of human alveolar bone regeneration with a porous tricalcium phosphate. A report of two cases. Clin Ora/ Implants Res. 12:379-384 (2001).

Zhang, et al., "Crystallization and microstructure analysis of calcium phosphate-based glass ceramics for biomedical applications," J. of Non-Crystalline Solids, 272 (2000) 14-21.

Bhadang, et al., "Influence of fluorapatite on the properties of thermally sprayed hydroxyapatite coatings," Biomaterials 25 (2004) 4935-4945.

Gibson, et al., "Phase Transformation of Tricalcium Phosphates Using High Temperature X-Ray Diffraction," Bioceramics vol. 9, 173-176 (1996).

Heughebaert, et al., "Physicochemical Characterization of Deposits Associated with HA Ceramics Implanted in Nonosseous Sites," J. Biomed. Mater. Res: Applied Biomaterials (1988) 22:A3, pp. 257-268.

Kawamura, et al., "Stimulatory effect of zinc-releasing calcium phosphate implant on bone formation in rabbit femora", J. Biomed. Mater. Res., 50 f21184-190 (2000).

Legeros, et al., "In Vivo Transformation of Biphasic Calcium Phosphate Ceramics: Ultrastructural and Physicochemical Characterizations," In: CRC Handbook of Bioactive Ceramics vol. II Calcium Phosphate and Hydroxylapatite Ceramics, Yamanuro T, Hench L, Wilson J, editors. Boca Raton: CRC Press, 1990, vol. 2, pp. 17-28.

Legeros, et al., "The effect of magnesium on the formation of apatites and whitlockites," In: Magnesium in Health and Disease, Y. Itokawa & J. Durlach, eds., London: John Libbey & Co Ltd.; 11 (1989), pp. 11-19.

Moreira-Gonzalez, et al., "Evaluation of 45S5 Bioactive Glass Combined as a Bone Substitute in the Reconstruction of Critical Size Calvarial Defects in Rabbits," The J. Craniofac. Surg., Jan. 2005, vol. 16, No. 1, pp. 63-70.

Mow, et al., Basic Orthopaedic Biomechanics and Mechano-Biology, Third Edition, pp. 123-519, Lippencott Williams & Wilkins, Philadelphia, 2005.

Oki, et al., "Preparation and in vitro bioactivity of zinc containing sol-gel-derived bioglass materials," J. Biomed. Mater. Res. 69A:216-221 (2004).

Shi, Biomaterials and Tissue Engineering, pp. 1-215, Spriner Berlin Heidelber, New York, 2004.

Vandenburgh, et al., "Mechanically induced alterations in cultured skeletal muscle growth," J. Biomech. (1991)24: Suppl. 1, pp. 91-99.

Yin, et al., "Density Functional Study of Structural, Electronic and Vibrational properties of Mg- and Zn-doped Tricalcium Phosphate Biomaterials", Biomaterials, 23 [20] 4155-4163 (2002).

Zhang, et al., "A Comparative Study of Electrochemical Deposition and Biomimetic Deposition of Calcium Phosphate on porous Titanium", Biomaterials; 26 f1612857-2865 (2005).

Y. I. Zawahreh. Effects of Ti02, Zr02 and Al203 dopants on the compressive strength of tricalcium phosphate (2005) Journal of Materials Science.

S. Yoshihara. Effects of glass composition on compressive strength of bioactive cement based on Ca0—Si02—P205 glass powders. (1993). Journal of Materials Science.

Office Action in U.S. Appl. No. 12/298,012 dated Feb. 28, 2013, 13 pages.

Office Action in U.S. Appl. No. 12/298,012 dated Nov. 7, 2013, 17 pages.

Saravanapavan, Bio-Medical Materials and Engineering, 14, 2004, IOS Press, pp. 467-486.

Office Action in U.S. Appl. No. 12/298,012 dated Feb. 25, 2014, 22 pages.

\* cited by examiner

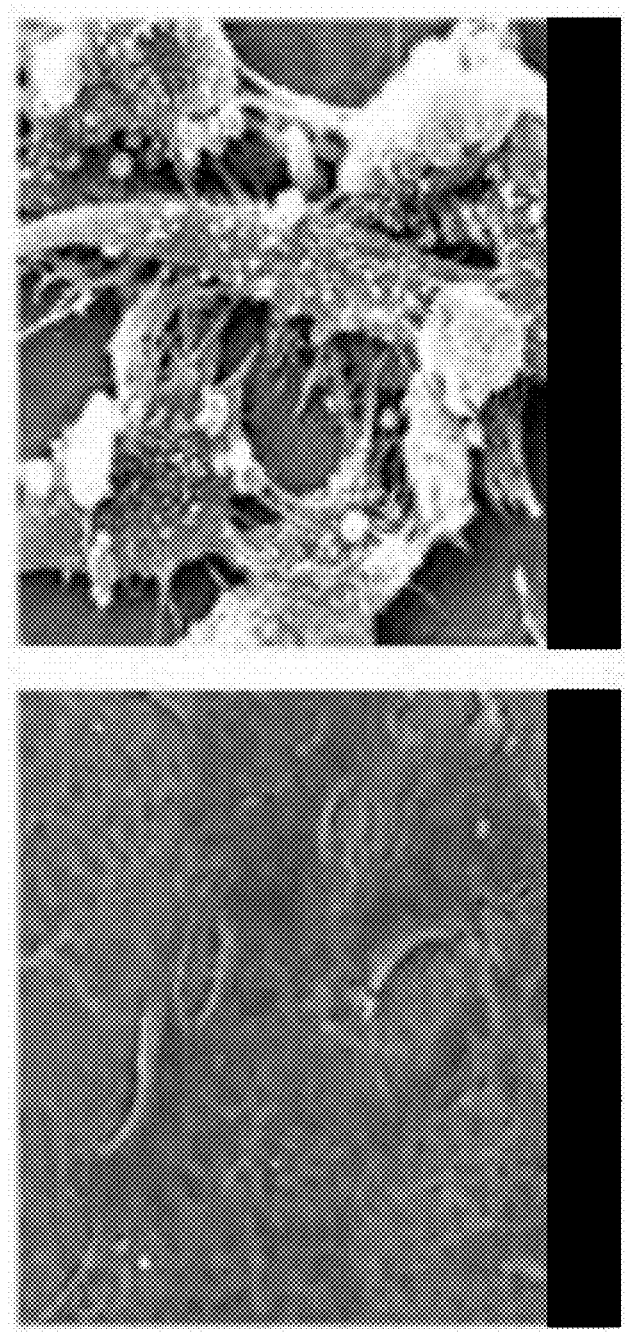

(A) Partial melting of metal powders leading to porous structures (B) Porous structure with designed porosity (C) Combinational approach (A+B)

BONE REPLACEMENT MATERIALS

CROSS-REFERENCE TO RELATED APPLICATIONS

This application is a divisional application of U.S. patent application Ser. No. 11/675,006, filed Feb. 14, 2007, which claims the benefit of priority to U.S. Provisional Patent Application Ser. No. 60/773,079, filed Feb. 14, 2006, and entitled "BONE REPLACEMENT MATERIALS," which in incorporated herein by reference in its entirety.

STATEMENT REGARDING FEDERALLY-SPONSORED RESEARCH

The invention was made with government support under the Office of Naval Research DURIP grant number 11F-3825-5131 and the Office of Naval Research grant numbers 3812-1001 and 3812-1003 (N00014-1-04-0644 and N00014-1-05-0583). The United States government may therefore have certain rights in the invention.

FIELD OF THE INVENTION

The invention described herein relates generally to bone and bone replacement materials, and more particularly to novel compositions and methods for the production of bone replacement materials having, inter alia, lower density and stiffness than prior art materials, and surface properties that enhance cellular adhesion and promote growth.

BACKGROUND

Musculoskeletal Disorders

Musculoskeletal disorders are recognized as among the most significant human health problems that exist today, costing society an estimated $254 billion every year, and afflicting one out of seven Americans. It is expected that the number of individuals with musculoskeletal disorders will increase over the coming years, as our population ages. Yet, in spite of the enormous magnitude of this problem, there is still a lack of bone replacement material that is appropriate for restoring lost structure and function, particularly for load bearing applications. This problem has resulted in a need for improved and mature biomaterials for load-bearing implants.

Natural synovial joints (e.g., hip, knee or shoulder joints) are complex and delicate structures capable of functioning under critical conditions. Their performance is due to the optimized combination of articular cartilage, a load-bearing connective tissue covering the bones involved in the joint, and synovial fluid, a nutrient fluid secreted within the joint area (Pillar '75; Mow '91). Unfortunately, human joints are prone to degenerative and inflammatory diseases that result in pain and joint stiffness. Primary or secondary osteoarthritis (osteoarthrosis), and to a lesser extent rheumatoid arthritis (inflammation of the synovial membrane) and condromalacia (softening of cartilage), are, apart from normal aging of articular cartilage, the most common degenerative processes affecting synovial joints (Dowson '92; Ardill '95). In fact, 90% of the population over the age of 40 suffers from some degree of degenerative joint diseases (Schumacher '88). Premature joint degeneration may arise from deficiencies in joint biomaterial properties, from excessive loading conditions, or from failure of normal repair processes. The explicit degenerative processes are not yet completely understood. Though minor surgical treatments are performed to provide temporary relief to ailing patients, the ultimate need is to replace the dysfunctional natural joints by ceramic, metal or polymer-based artificial materials by means of what is known in the art as 'total joint replacement' (TJR) surgery.

Stress Shielding

Bones in normal, healthy condition carry external joint and muscular loads by themselves. Following the insertion of orthopedic screws/implants, the treated bone will share its load-carrying capacity with the screws/implants. Thus the same load that had been originally born by the bone itself will now be carried by the 'composite' new structure. For load bearing screws and implants, the clinically available devices are metallic and therefore significantly stiffer (elastic modulus of around 110 GPa for titanium and over 200 GPa for steel) than the adjacent bone (modulus of 1-20 GPa), and internal loads will mainly be supported by the screws that are now 'shielding' the bone from carrying the normal mechanical stresses. This 'stress shielding' effect alters the normal stress stimuli for bone growth, and in accordance with Wolff's law, the reduction of bone stresses relative to the natural situation causes bone to adapt itself by reducing its mass in a process of resorption around the implant. The relationship between implant flexibility and the extent of bone loss has been established in clinical patient series and animal experiments and confirm that changes in bone morphology are an effect of stress shielding and a subsequent adaptive remodeling process. This resorption/bone loss effect will cause micromotion of the screws/implants in response to external loads and could further damage the interfacing bone layer and anchorage performances subsequent to possible loosening of the screw/implant (Gefen '02). Early loosening of the screws/implants can not only delay or damage the healing process, but can also endanger adjacent anatomical structures and can even require surgery for the immediate removal of the failed implants (Lowery '98). Such aspects inevitably impose a prolonged and painful rehabilitation process on patients, as well as substantial treatment costs. Animal (e.g., canine) experiments with screw and plate fixation systems have shown that cortical and trabecular bone losses are reduced if a reduced-stiffness implants with identical geometrical designs are used (Pillar '79; Tomita '87).

Choice of Materials for Orthopedic Implants

The choice of material for each component of such an implant depends on the design, size and required strength of the system. For total hip (THR) and total knee (TKR) joint replacements surgeries, metals are considered as the best candidate due to their higher load bearing capabilities and higher fatigue resistance (Cohen '79). The requirements for modern day metallic implants, especially for total joint replacement can be broadly categorized as follows (Hoeppner '94): (1) superior biocompatibility between the material and surrounding environment with no adverse cytotoxicity and tissue reaction; and (2) the mechanical and physical properties necessary to achieve the desired function. Some desired properties are, for example, low modulus, high strength, good ductility, excellent corrosion resistance in the body fluid medium, high fatigue strength and good wear resistance.

The above criteria are met by only a handful of metals and alloys. In the past, only stainless steel (e.g., 316 and 316L)

and cobalt based alloys (e.g., CoCrMo) were considered suitable for metallic implants. Wrought and lightly cold-worked 316 stainless steels are even now used for making the femoral component in the art-recognized 'trapeziodal-28 total hip replacement' surgery. Likewise, the femoral component of the art-recognized 'total Condylar Prosthesis' of the knee is made from the investment casting of the Cobalt Stellite 21 alloy. However, titanium and its alloys started gaining popularity as implant materials in the early 1970's because to their lower modulus, superior tissue compatibility and better corrosion resistance (Dowson '92).

Titanium and its alloys have been widely used for orthopedic and dental implant applications primarily due to their excellent combination of enhanced strength, lower modulus, good ductility, enhanced corrosion resistance, and good biocompatibility as compared with stainless steels and cobalt-based alloys. Commercially pure (cp) titanium was the first to be used. Though cp-Ti exhibited better corrosion resistance and tissue tolerance as compared to stainless steel, cp-Ti's rather limited strength confined its applicability to specific parts such as hip cup shells, dental crown and bridges, endosseous dental implants, pacemaker cases and heart valve cages (Wang '96; Lee '02). However, while the use of titanium-based alloys has been quite beneficial for such implants, high stiffness and high density of the alloy compared to natural bone is still a problem causing 'stress-shielding.' To improve the strength for load bearing applications such as total joint replacements, the alloy Ti-6Al-4V ELI (i.e., with extra low interstitial impurity content) was chosen as a candidate biomaterial for surgical implants in the late 1970's. Ti-6Al-4V is one of the most widely used Ti alloys and exhibits excellent corrosion resistance, low density, good biocompatibility, and excellent mechanical properties, including high strength and low modulus. Ti-6Al-4V has an elastic modulus of ~110 GPa that is only about half that of 316L stainless steel (~200 GPa) and CoCrMo alloys (~210 GPa). The mechanical properties of Ti-6Al-4V are critically dependent on its microstructure and can consequently be tailored by thermo-mechanical processing.

Porous Metals

Despite the great progress that has been achieved in orthopedic biomaterials, fixation of implants to the bone host remains a problem. Mismatch of Young's moduli of the biomaterials and the surrounding bone has been identified as a major reason for implant loosening following stress shielding of bone (Robertson '76). However, the implanted material must be strong enough and durable to withstand the physiological loads placed upon it over the years. A suitable balance between strength and stiffness has to be found to best match the behavior of bone. One consideration to achieve this has been the development of materials that exhibit substantial surface or total bulk porosity in medical applications. The fabrication of porous materials for biomedical applications has been actively researched since 1972 (Weber '72) in which osseointegration was shown in porous metals. Numerous investigations into porous materials where subsequently initiated involving porous ceramic, polymeric, and other metallic materials. Although ceramics portray excellent corrosion resistance, they cannot be employed as load bearing implants due to their inherent brittleness. Similarly, porous polymeric systems cannot sustain the mechanical forces present in joint replacement surgery. This led researchers to focus on porous metals, based on orthopedic metallic materials, as a consequence of their superior fracture and fatigue resistance characteristics, which are required for load-bearing applications. Ryan et al. recently published an excellent review on this subject (Ryan '06).

Boblyn et al. (Boblyn '90) performed an experiment on bilateral non-cemented total hip arthroplasties in canine models to determine the effect of stem stiffness on stress-related bone resorption. Two partly porous femoral implants of substantially different stiffness were designed for direct comparison. One was manufactured from Co—Cr alloy, the other from titanium alloy, but modified internally by drilling a hole that extended from the stem tip to within 5 mm of the shoulder, which transformed it into a hollow cylinder. Femora with the flexible stems consistently showed much less bone resorption than those with the stiff stems. Quantitative analysis of paired cross-sections indicated an average of 25-35% more cortical bone area in femora that received low stiffness hollow cylindrical stems.

Titanium and its alloy (Ti6Al4V) have elastic moduli less than 50% of that in Co—Cr implants so that their use would help reduce the extent of stress shielding. Although fabrication of implants from materials with lower elastic moduli can reduce stress shielding the stiffness mismatch to bone is still substantial (Otani '92). The clinical literature of the past 30 years records a variety of approaches to this end and several researchers have performed studies aimed at clarifying the fundamental aspects of interactions between porous metals and hard tissue.

Surface Modification of Load Bearing Metal Implants

Surface modification is a common approach to increase bioactivity of load bearing metal implants. Either metal on metal or hydroxyapatite based ceramic coatings are most common. These coatings are commonly applied to metal surfaces using thermal spraying techniques such as plasma spraying, flame spraying, and high-velocity oxy-fuel (HVOF) combustion spraying (Berndt, '90). Reproducibility and economic efficiency of the thermal spraying techniques have an outstanding advantage. However, these methods present poor coating-substrate adherence and lack of uniformity of the coating in terms of morphology and crystallinity (Brossa, '93). In clinical applications, HA coatings prepared by plasma spraying techniques were found to 'flake away' from the surface of substrate surface after implantation in the body (Berndt, '90).

SUMMARY OF THE INVENTION

Particular aspects provide novel load-bearing implants with reduced effective stiffness and density that can facilitate reduced 'stress shielding' during in vivo applications. In certain aspects implants are designed to comprise porosity, and are fabricated using a rapid prototyping technique. Particular aspects provide smart designs and advanced manufacturing methods in producing hollow implants with reduced effective stiffness and effective density.

Certain exemplary aspects provide a hollow hip-stem in which the porosity is closed, which can reduce the effective stiffness and density by 30 to 50% compared to a more traditional dense implant. In additional embodiments, the porosity is connected from the outside surface for guided tissue integration to improve biological bonding.

In particular aspects, the inventive structures are produced using a laser engineered net shaping (LENS™) process, and such exemplary LENS™ fabricated structures (e.g., FIG. 1) have been tested for their physical, mechanical and biological properties. Assuming a simple cylindrical design, for example, a large internal porosity can reduce the material volume by 30 to 50%, which can reduce the effective modulus by 30 to 50% (assuming a linear rule of mixture).

In particular aspects, the inventive implants solve long-standing problems in the art of load bearing metal implants. For example, traditional total hip replacements (THR) a dense metal is used that has significantly higher density, stiffness and strength than natural bone, which is a naturally porous material, and typical lifetimes of such THRs are only seven to twelve years; a lifetime that has remained constant over the past fifty years until the present invention. According to particular aspects, developing materials and structures with properties similar to natural bone provides a solution to increasing the lifetime of load bearing implants.

In additional aspects, the surface bioactivity of the LENS™ fabricated implants is increased by surface modification with nano-porous materials. Utilizing bioactive materials and intelligent surface modification increases early stage cell adhesion, and enhance cellular proliferation ultimately resulting in faster healing.

Particular aspects provide a device for bone tissue engineering, comprising a metal or metal-based composite member/material comprising an interior macroporous structure in which porosity may vary from 0-90 vol % (or from about 3% to about 90%, about 5% to about 85%, about 10% to about 90%, about 15% to about 90%, about 20% to about 90%, about 25% to about 90%, about 30% to about 90%, about 40% to about 90%, about 50% to about 90%, about 60% to about 90%, about 75% to about 90%, about 5% to about 75%, about 5% to about 50%, about 5% to about 40%, about 5% to about 30% about 5% to about 25%), the member comprising a surface region having a surface pore size, porosity, and composition designed to encourage cell growth and adhesion thereon, to provide a device suitable for bone tissue engineering in a recipient subject. In certain embodiments, the device comprises a gradient of pore size, porosity, and material composition extending from the surface region into or throughout the interior of the device, wherein the gradient transition is continuous or seamless and the growth of cells extending from the surface region inward is promoted. In particular embodiments, the member/material comprises at least one material selected from the group consisting of: titanium (Ti); commercially pure Ti; alpha Ti alloys; beta Ti alloys; aluminum (Al); iron (Fe); vanadium (V)); Ti alloys and their intermetallics with major alloying elements including Al, V, Nb, Fe, Zr, Mo, O, Ni, Cr, Co; Ta forming alloys including Ti6Al4V, Ti-6Al-7Nb, Ti-5Al-2.5Fe, Ti-12Mo-6Zr-2Fe, Ti-15Mo-5Zr-3Al, Ti-15Mo-3Nb-3O, Ti-13Nb-13Zr, Ti-35Nb-5Ta-7Zr; Stainless steel, CoCrMO; ceramics, metal oxides including $TiO_2$, calcium based inorganic salt including calcium phosphates, calcium carbonates, silver and silver oxides, gold, and combinations thereof. In certain aspects, the composite member/material or a portion of the surface region thereof comprises a material composition of metal and ceramic in a gradient or continuous or seamless gradient from a position on the exterior surface having a highest ceramic content, transitioning to lowest or zero ceramic content at an interior structure position composed of metal or metal-based composite. In certain embodiments, the ceramic portion comprises an inorganic salt. In particular aspects, the inorganic salt comprises a form of calcium selected from the group consisting of calcium phosphates and calcium carbonates, and combinations thereof. In particular embodiments, the surface region comprises nanoscale or microscale pores ranging from about 1 nm to about 500 nm in diameter, or from about 1 nm to about 1 µm. In certain implementations, the member/material structure comprises a microporous or macroporous pattern having pore sizes in the range of about 1 µm to about 5 mm. In certain embodiments, the method comprises depositing a chemical or biological agent deposited in or on the composite member/material or in one or more pores thereof to operatively provide for release or controlled release of the agent within a recipient. In certain embodiments, the chemical or biological agent is deposited in or on one or more surface structures or pores thereof. In certain aspects, the agent comprises at least one agent suitable to provide a beneficial biological or physiological effect. In particular embodiments, the at least one agent suitable to provide a beneficial biological or physiological effect comprises an antimicrobial agent. In certain embodiments, the agent comprises at least one agent selected from the group consisting of antibiotics, growth factors, and drugs. In particular embodiments, at least one of the pore size, porosity and material composition is selected to provide a device having an optimal density, elastic modulus or compression strength for a specific recipient. In certain aspects, the macroporous structure is selected to provide a device having an optimal density, elastic modulus or compression strength for a specific recipient.

Additional aspects provide a device for bone tissue engineering, comprising a metal or metal-based composite member/material comprising an interior porous structure, wherein at least one of the pore size, porosity and material composition is selected to provide a device having an optimal density for a specific recipient.

Additional embodiments provide a device for bone tissue engineering, comprising a metal or metal-based composite member/material comprising an interior porous structure, wherein at least one of the pore size, porosity and material composition is selected to provide a device having an optimal elastic modulus for a specific recipient.

Yet additional embodiments provide a device for bone tissue engineering, comprising a metal or metal-based composite member/material comprising an interior porous structure, wherein at least one of the pore size, porosity and material composition is selected to provide a device having an optimal compression strength for a specific recipient.

Further embodiments provide a method of producing a porous metal or metal-based composite device for bone tissue engineering, comprising: obtaining input from bone imaging scans of a specific patient to provide input data; entering the input data or values derived therefrom into a fabrication machine; fabricating a porous bone tissue engineering device with the fabrication machine based on the input data, wherein at least one of the density, the modulus of elasticity and the compression strength of the member/material is selected to provide a device having at least one of an optimal density, elastic modulus and compression strength for a specific recipient. In certain aspects, the device comprises surface modifications to encourage cell growth and adhesion thereon. In particular embodiments, the fabrication machine consists of or comprises a Laser Engineered Net Shaping (LENS) apparatus. In certain implementations of the method, fabrication comprises fabrication of a device comprising a porous metal or metal-based composite. Additional embodiments provide a device for bone tissue engineering formed by these methods.

Yet additional aspects provide a method of producing a device for bone tissue engineering, comprising: selecting a solid freeform fabrication technique; and fabricating, using the fabrication technique, a metal or metal-based composite member/material comprising an interior macroporous structure in which porosity may vary from 0-90 vol % (or from about 3% to about 90%, about 5% to about 85%, about 10% to about 90%, about 15% to about 90%, about 20% to about 90%, about 25% to about 90%, about 30% to about 90%, about 40% to about 90%, about 50% to about 90%, about 60% to about 90%, about 75% to about 90%, about 5% to about 75%, about 5% to about 50%, about 5% to about 40%, about 5% to about 30% about 5% to about 25%), wherein the member/material comprises a surface region having at lease one of a surface pore size, porosity, and composition designed to encourage cell growth and adhesion thereon, to provide a device suitable for bone tissue engineering in a recipient subject. In certain embodiments, the method comprises making a gradient of pore size, porosity, and material composition extending from the surface region into or throughout the interior of the device, wherein the gradient transition is continuous or seamless and suitable to operatively promote the growth of cells extending from the surface region inward. In certain aspects, the member/material comprises at least one material selected from the group consisting of: titanium (Ti); commercially pure Ti; alpha Ti alloys; beta Ti alloys; aluminum (Al); iron (Fe); vanadium (V)); Ti alloys and their intermetallics with major alloying elements including Al, V, Nb, Fe, Zr, Mo, O, Ni, Cr, Co; Ta forming alloys including Ti6Al4V, Ti-6Al-7Nb, Ti-5Al-2.5Fe, Ti-12Mo-6Zr-2Fe, Ti-15Mo-5Zr-3Al, Ti-15Mo-3Nb-3O, Ti-13Nb-13Zr, Ti-35Nb-5Ta-7Zr; Stainless steel, CoCrMO; ceramics, metal oxides including $TiO_2$, calcium based inorganic salt including calcium phosphates, calcium carbonates, silver and silver oxides, gold, and combinations thereof. In certain embodiments, the freeform fabrication technique consists of or comprises Laser Engineered Net Shaping (LENS). In particular embodiments, the surface region comprises nanoscale or microscale pores ranging from about 1 nm to about 500 nm in diameter, or from about 1 nm to about 1 μm diameter, suitable to operatively facilitate cell growth and/or adhesion thereon. In particular aspects, the surface region comprising the nanoscale or microscale pores is positioned to be operatively in contact with or be inserted into a bone upon implant of the member/material. In particular embodiments, the surface region comprising the nanoscale or microscale pores is fabricated by electrochemical etching and/or chemical dissolution, which may be preformed simultaneously or in sequence. In certain implementations, the composite member/material or a portion of the surface region thereof comprises a material composition of metal and ceramic in a gradient or continuous or seamless gradient from a position on the exterior surface having a highest ceramic content, transitioning to lowest or zero ceramic content at an interior structure position composed of metal or metal-based composite. In certain aspects, the ceramic portion comprises an inorganic salt. In particular embodiments, the inorganic salt comprises a form of calcium selected from the group consisting of calcium phosphates and calcium carbonates, and combinations thereof. In particular embodiments, the member/material structure comprises a microporous or macroporous pattern having pore sizes in the range of about 1 μm to about 5 mm. In certain embodiments, the method comprises depositing a chemical or biological agent in or on the composite member/material or in one or more pores thereof to operatively provide for release or controlled release of the agent within a recipient. In certain aspects, the chemical or biological agent is deposited in or on one or more surface structures or pores thereof. In particular implementations, the agent comprises at least one agent suitable to provide a beneficial biological or physiological effect. In certain aspects, the at least one agent suitable to provide a beneficial biological or physiological effect comprises an antimicrobial agent. In particular embodiments, the agent comprises at least one agent selected from the group consisting of antibiotics, growth factors, and drugs.

BRIEF DESCRIPTION OF THE DRAWINGS

FIG. 1A hollow cylinder from out-side. FIGS. 1B and 1C show possible cross-sectional views of internal porosity, closed hollow porosity or connected porosity for guided tissue regeneration and FIG. 1D shows a longitudinal view of the cylinder with porosity in FIG. 1B.

FIGS. 9A-9B show, according to particular exemplary aspects of the present invention, OPC1 cells on nano-porous TiO2 surface after (a) 3 days and (b) 11 days, respectively. Comparison of the OPC1 cell attachment on 4 h anodized surface up to 11 days. Excellent cell attachment and proliferation was observed in which microextensions projecting out from the cellular region to the anodized surface could be seen. On the 11-day sample, small calcified nodule as a sign for differentiation is observed.

FIG. 10A shows etched surface in the middle shows significantly less cell attachment after 7 days in cell culture. FIG. 10B shows high magnification picture of OPC1 cells on $TIO_2$ surface. FIG. 10C shows high magnification picture of surface from which nano-porous $TiO_2$ was etched off. Significantly poor cell attachment can be noticed in (c) compared to (b). It is clear from the figure that preferential cell attachment took place in regions where nano-porous $TiO_2$ was present. This significant improvement in cell attachment in the nano-porous area over bare Ti surface clearly shows that nano-porous $TiO_2$ improves cell-materials interactions, such as cell-adhesion and growth.

DETAILED DESCRIPTION OF THE INVENTION

Figure 1A:
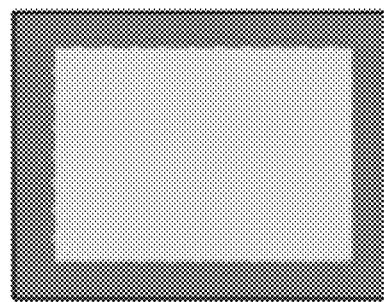
FIGS. 1A-1D show exemplary design and fabrication structures according to particular exemplary aspects of the present invention.
Figure 1B:
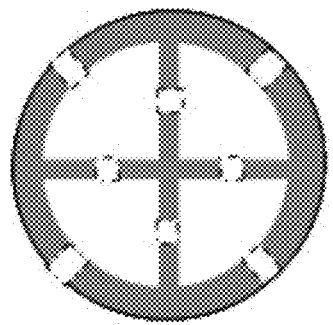

Aspects of the present invention provide methods for producing bone replacement materials with lower density, lower stiffness and enhanced cellular adhesion. In particular embodiments, the bone replacement compositions comprise materials including, but not limited to: metals (e.g. titanium (commercially pure Ti, and both α and β alloys), aluminum (Al), iron (Fe), vanadium (V)); metal alloys (e.g., Ti alloys with major alloying elements such as Al, V, Nb, Fe, Zr, Mo, O, Ni, Cr, Co, Ta forming alloys such as Ti6Al4V, Ti-6Al-7Nb, Ti-5Al-2.5Fe, Ti-12Mo-6Zr-2Fe, Ti-15Mo-5Zr-3Al, Ti-15Mo-3Nb-3O, Ti-13Nb-13Zr, Ti-35Nb-5Ta-7Zr, Stainless steel, CoCrMO); metal oxides (e.g., $TiO_2$), ceramics, inorganic salts (e.g., such as different forms of calcium phosphates and calcium carbonates and their combinations); polymeric materials and/or combinations thereof may be employed. According to particular aspects, the density of the material can be decreased through production of bone replacement materials with hollow cores.

Particular embodiments provide macro porous (0.1-10 cm) structures, wherein the core of the bulk material is comprised of a geometric pattern of material with voided areas to provide low density structures with a quazi-solid exteriors.

Certain embodiments comprise meso-scale (0.1-10 mm) pores in the exterior walls of the bone replacement materials, wherein the pores open to the voided areas within the core of the material.

Additional aspects provide methods to produce nanoscale (1-10,000 nm) pores on the internal and external surfaces of the material, wherein the material surface is altered by simultaneous electrochemical etching and/or chemical dissolution, which may be preformed simultaneously or in sequence.

Further aspects provide materials facilitating enhanced cellular adhesion, wherein cell (e.g., osteoblast, fibroblast, muscle, chondrocytes) growth and adhesion occurs preferentially on nanoporous surfaces.

Additional embodiments comprise positioning/storage of chemical agents within the nanoporous surfaces, wherein the agents produce effects beneficial for biological applications (e.g., antibiotics, growth factors, drugs).

Specific exemplary manifestations of this invention are provided herein as illustrations and are not intended to limit the scope of the claimed invention as various modifications will become apparent to one skilled in the art given the enabling teachings herein.

Particular Exemplary Preferred Embodiments:

Particular aspects provide a device for bone tissue engineering, comprising a metal or metal-based composite member/material comprising an interior macroporous structure in which porosity may vary from 0-90 vol % (or from about 3% to about 90%, about 5% to about 85%, about 10% to about 90%, about 15% to about 90%, about 20% to about 90%, about 25% to about 90%, about 30% to about 90%, about 40% to about 90%, about 50% to about 90%, about 60% to about 90%, about 75% to about 90%, about 5% to about 75%, about 5% to about 50%, about 5% to about 40%, about 5% to about 30% about 5% to about 25%), the member comprising a surface region having a surface pore size, porosity, and composition designed to encourage cell growth and adhesion thereon, to provide a device suitable for bone tissue engineering in a recipient subject. In certain embodiments, the device comprises a gradient of pore size, porosity, and material composition extending from the surface region into or throughout the interior of the device, wherein the gradient transition is continuous or seamless and the growth of cells extending from the surface region inward is promoted. In particular embodiments, the member/material comprises at least one material selected from the group consisting of: titanium (Ti); commercially pure Ti; alpha Ti alloys; beta Ti alloys; aluminum (Al); iron (Fe); vanadium (V)); Ti alloys and their intermetallics with major alloying elements including Al, V, Nb, Fe, Zr, Mo, O, Ni, Cr, Co; Ta forming alloys including Ti6Al4V, Ti-6Al-7Nb, Ti-5Al-2.5Fe, Ti-12Mo-6Zr-2Fe, Ti-15Mo-5Zr-3Al, Ti-15Mo-3Nb-3O, Ti-13Nb-13Zr, Ti-35Nb-5Ta-7Zr; Stainless steel, CoCrMO; ceramics, metal oxides including $TiO_2$, calcium based inorganic salt including calcium phosphates, calcium carbonates, silver and silver oxides, gold, and combinations thereof. In certain aspects, the composite member/material or a portion of the surface region thereof comprises a material composition of metal and ceramic in a gradient or continuous or seamless gradient from a position on the exterior surface having a highest ceramic content, transitioning to lowest or zero ceramic content at an interior structure position composed of metal or metal-based composite. In certain embodiments, the ceramic portion comprises an inorganic salt. In particular aspects, the inorganic salt comprises a form of calcium selected from the group consisting of calcium phosphates and calcium carbonates, and combinations thereof. In particular embodiments, the surface region comprises nanoscale or microscale pores ranging from about 1 nm to about 500 nm in diameter, or from about 1 nm to about 1 µm. In certain implementations, the member/material structure comprises a microporous or macroporous pattern having pore sizes in the range of about 1 µm to about 5 mm. In certain embodiments, the method comprises depositing a chemical or biological agent deposited in or on the composite member/material or in one or more pores thereof to operatively provide for release or controlled release of the agent within a recipient. In certain embodiments, the chemical or biological agent is deposited in or on one or more surface structures or pores thereof. In certain aspects, the agent comprises at least one agent suitable to provide a beneficial biological or physiological effect. In particular embodiments, the at least one agent suitable to provide a beneficial biological or physiological effect comprises an antimicrobial agent. In certain embodiments, the agent comprises at least one agent selected from the group consisting of antibiotics, growth factors, and drugs. In particular embodiments, at least one of the pore size, porosity and material composition is selected to provide a device having an optimal density, elastic modulus or compression strength for a specific recipient. In certain aspects, the macroporous structure is selected to provide a device having an optimal density, elastic modulus or compression strength for a specific recipient.

Additional aspects provide a device for bone tissue engineering, comprising a metal or metal-based composite member/material comprising an interior porous structure, wherein at least one of the pore size, porosity and material composition is selected to provide a device having an optimal density for a specific recipient.

Additional embodiments provide a device for bone tissue engineering, comprising a metal or metal-based composite member/material comprising an interior porous structure, wherein at least one of the pore size, porosity and material composition is selected to provide a device having an optimal elastic modulus for a specific recipient.

Yet additional embodiments provide a device for bone tissue engineering, comprising a metal or metal-based composite member/material comprising an interior porous structure, wherein at least one of the pore size, porosity and material composition is selected to provide a device having an optimal compression strength for a specific recipient.

Further embodiments provide a method of producing a porous metal or metal-based composite device for bone tissue engineering, comprising: obtaining input from bone imaging scans of a specific patient to provide input data; entering the input data or values derived therefrom into a fabrication machine; fabricating a porous bone tissue engineering device with the fabrication machine based on the input data, wherein at least one of the density, the modulus of elasticity and the compression strength of the member/material is selected to provide a device having at least one of an optimal density, elastic modulus and compression strength for a specific recipient. In certain aspects, the device comprises surface modifications to encourage cell growth and adhesion thereon. In particular embodiments, the fabrication machine consists of or comprises a Laser Engineered Net Shaping (LENS) apparatus. In certain implementations of the method, fabrication comprises fabrication of a device comprising a porous metal or metal-based composite. Additional embodiments provide a device for bone tissue engineering formed by these methods.

Yet additional aspects provide a method of producing a device for bone tissue engineering, comprising: selecting a solid freeform fabrication technique; and fabricating, using the fabrication technique, a metal or metal-based composite member/material comprising an interior macroporous structure in which porosity may vary from 0-90 vol % (or from about 3% to about 90%, about 5% to about 85%, about 10% to about 90%, about 15% to about 90%, about 20% to about 90%, about 25% to about 90%, about 30% to about 90%, about 40% to about 90%, about 50% to about 90%, about 60% to about 90%, about 75% to about 90%, about 5% to about 75%, about 5% to about 50%, about 5% to about 40%, about 5% to about 30% about 5% to about 25%), wherein the member/material comprises a surface region having at lease one of a surface pore size, porosity, and composition designed to encourage cell growth and adhesion thereon, to provide a device suitable for bone tissue engineering in a recipient subject. In certain embodiments, the method comprises making a gradient of pore size, porosity, and material composition extending from the surface region into or throughout the interior of the device, wherein the gradient transition is continuous or seamless and suitable to operatively promote the growth of cells extending from the surface region inward. In certain aspects, the member/material comprises at least one material selected from the group consisting of: titanium (Ti); commercially pure Ti; alpha Ti alloys; beta Ti alloys; aluminum (Al); iron (Fe); vanadium (V)); Ti alloys and their intermetallics with major alloying elements including Al, V, Nb, Fe, Zr, Mo, O, Ni, Cr, Co; Ta forming alloys including Ti6Al4V, Ti-6Al-7Nb, Ti-5Al-2.5Fe, Ti-12Mo-6Zr-2Fe, Ti-15Mo-5Zr-3Al, Ti-15Mo-3Nb-3O, Ti-13Nb-13Zr, Ti-35Nb-5Ta-7Zr; Stainless steel, CoCrMO; ceramics, metal oxides including $TiO_2$, calcium based inorganic salt including calcium phosphates, calcium carbonates, silver and silver oxides, gold, and combinations thereof. In certain embodiments, the freeform fabrication technique consists of or comprises Laser Engineered Net Shaping (LENS). In particular embodiments, the surface region comprises nanoscale or microscale pores ranging from about 1 nm to about 500 nm in diameter, or from about 1 nm to about 1 µm diameter, suitable to operatively facilitate cell growth and/or adhesion thereon. In particular aspects, the surface region comprising the nanoscale or microscale pores is positioned to be operatively in contact with or be inserted into a bone upon implant of the member/material. In particular embodiments, the surface region comprising the nanoscale or microscale pores is fabricated by electrochemical etching and/or chemical dissolution, which may be preformed simultaneously or in sequence. In certain implementations, the composite member/material or a portion of the surface region thereof comprises a material composition of metal and ceramic in a gradient or continuous or seamless gradient from a position on the exterior surface having a highest ceramic content, transitioning to lowest or zero ceramic content at an interior structure position composed of metal or metal-based composite. In certain aspects, the ceramic portion comprises an inorganic salt. In particular embodiments, the inorganic salt comprises a form of calcium selected from the group consisting of calcium phosphates and calcium carbonates, and combinations thereof. In particular embodiments, the member/material structure comprises a microporous or macroporous pattern having pore sizes in the range of about 1 µm to about 5 mm. In certain embodiments, the method comprises depositing a chemical or biological agent in or on the composite member/material or in one or more pores thereof to operatively provide for release or controlled release of the agent within a recipient. In certain aspects, the chemical or biological agent is deposited in or on one or more surface structures or pores thereof. In particular implementations, the agent comprises at least one agent suitable to provide a beneficial biological or physiological effect. In certain aspects, the at least one agent suitable to provide a beneficial biological or physiological effect comprises an antimicrobial agent. In particular embodiments, the agent comprises at least one agent selected from the group consisting of antibiotics, growth factors, and drugs.

Example 1

Laser Engineered Net Shaping (LENS™) and Developing Macro-Porous Structures

Figure 2:
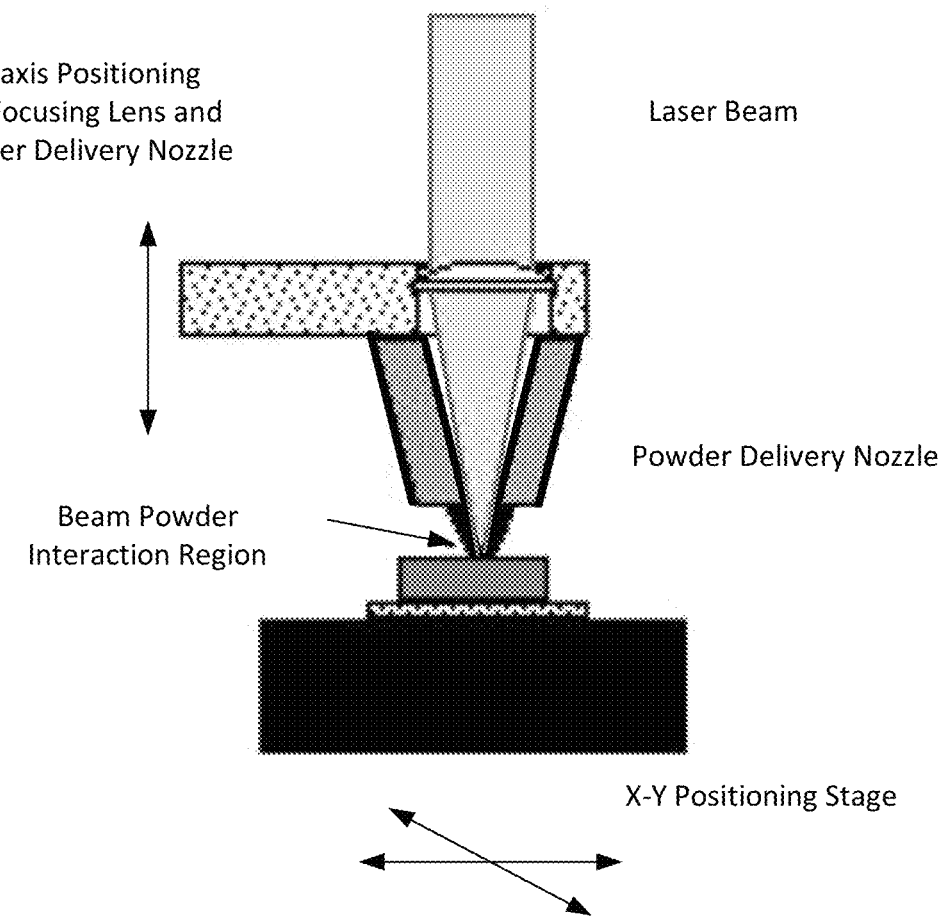
FIG. 2 shows, according to particular exemplary aspects of the present invention, a schematic representation of a LENS™ process for making the inventive implants.

Unlike many existing rapid prototyping (RP) methods, the LENS™ technology uses metal powders to create functional parts that can be used in numerous applications. A schematic representation of an exemplary LENS™ process for providing the inventive implants is depicted in FIG. 2. Briefly, a LENS 750 machine uses 500 W of Nd:YAG laser power focused onto a metal substrate to create a molten puddle on the substrate surface. Metal powder is then injected into the molten puddle to increase the material volume. The substrate is then scanned relative to the deposition apparatus to write lines of the metal with a finite width and thickness. Rastering of the part back and forth to create a pattern and fill where material is required allows a layer of material to be deposited. Finally, this procedure is repeated many times until the entire object represented in the three-dimensional CAD model is produced on the machine. In this fashion, a fully dense part is built up from its powders. This approach to producing a mechanical component in a layer-by-layer fashion allows the user to fabricate the part with features that cannot be readily reproduced by other methods. Using an appropriate combination of processing parameters, solidification rates of ~$10^3$ to $10^5$ K/sec can be achieved in LENS™ processing. Such rapid solidification conditions also allow for the formation of fine-grained, chemically homogeneous microstructures with excellent mechanical properties.

Figure 3:
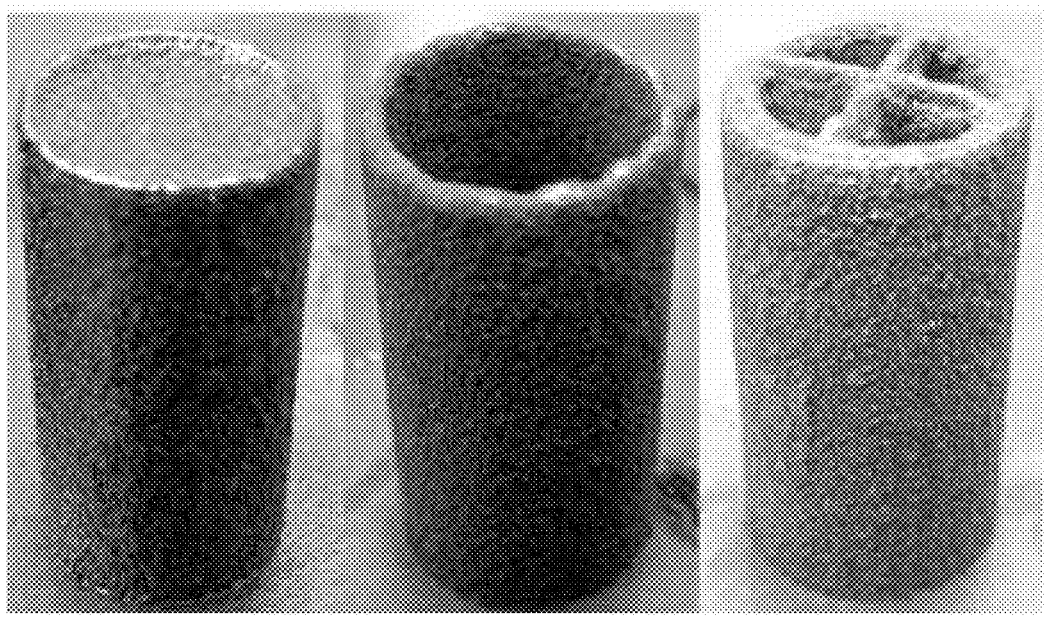
FIG. 3 shows, according to particular exemplary aspects of the present invention, LENS™ processed cylindrical parts of 5 cm height and 2.5 cm diameter. LENS™ processed cp-Ti cylindrical parts: fully dense, tubular and designed porosity.

FIG. 3 shows LENS™ processed cylindrical parts of 5 cm height and 2.5 cm diameter, which was fabricated according to applicants' inventive specifications.

Figure 4:
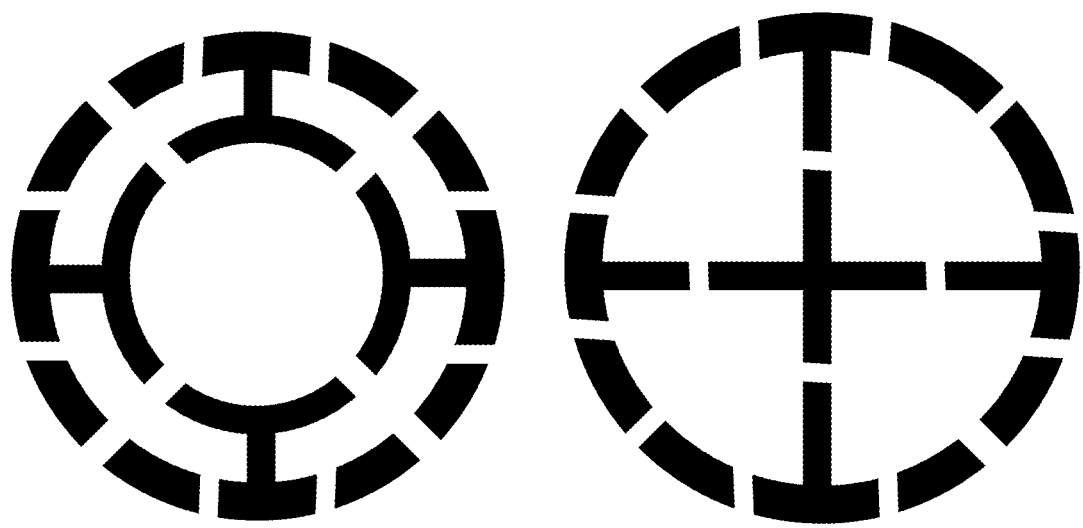
FIG. 4 shows, according to particular exemplary aspects of the present invention, exemplary internal geometries. Exemplary designs of load-bearing metal implants with porosity for guided tissue engineering.

FIG. 4 shows exemplary internal geometries according to particular inventive aspects. Good geometry control (±0.05 mm) and surface finish were achieved. Commercially pure Ti (cp Ti) powder with particle size range 50-150 µm was used to fabricate these structures. The Z-increment and hatch spacing were 0.25 and 0.38 mm, respectively. These samples were fabricated using a laser power of 420 W, and scan speeds were varied between 17-21 mm/sec with a powder feed rate of 11 g/min. These exemplary structures show that parts with different internal porosity can be fabricated using the inventive approach.

Figure 5:
FIG. 5 shows, according to particular exemplary aspects of the present invention, two LENS™ fabricated Ti6Al4V hip-stems with overhang above 30°. Hollow and Dense/solid hip-stems using LENS™.

FIG. 5 shows two inventive LENS™ fabricated Ti6Al4V hip-stems with overhang above 30°. One of the hip-stems has closed internal porosity to reduce mass and effective stiffness. These hip-stems were fabricated using 420 W laser power, scan speed in the range of 15-17 mm/s and powder feed rate 11-14 g/min. A total build time between 1-4 hr was needed to for the fabrication of each of these parts (depending on porosity). The weight of the fully dense hip-stem is 180 g, while the hip-stem with internal porosity weighs only 70 g. A 61% weight reduction was achieved in this particular structure made with Ti6Al4V.

Figure 11:
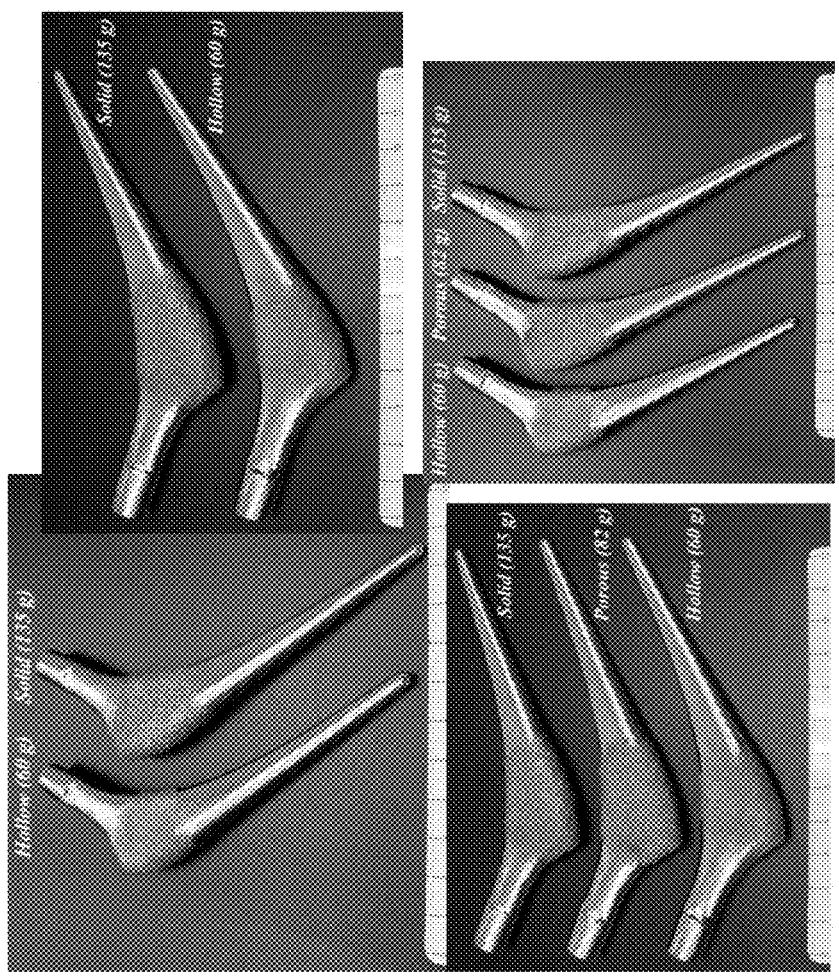
FIG. 11 shows, according to particular exemplary aspects of the present invention, inventive surface-finished hip stems produced via LENS™, which clearly shows that post-processing of processed parts are within the present inventive scope. The microstructure of the LENS processed alloys was found to be influenced by laser power, scan speed or powder feed rate.

FIG. 11 shows inventive surface-finished hip stems produced via LENS™, which clearly shows that post-processing of processed parts are within the present inventive scope. The microstructure of the LENS processed alloys was found to be influenced by laser power, scan speed or powder feed rate.

Figure 6:
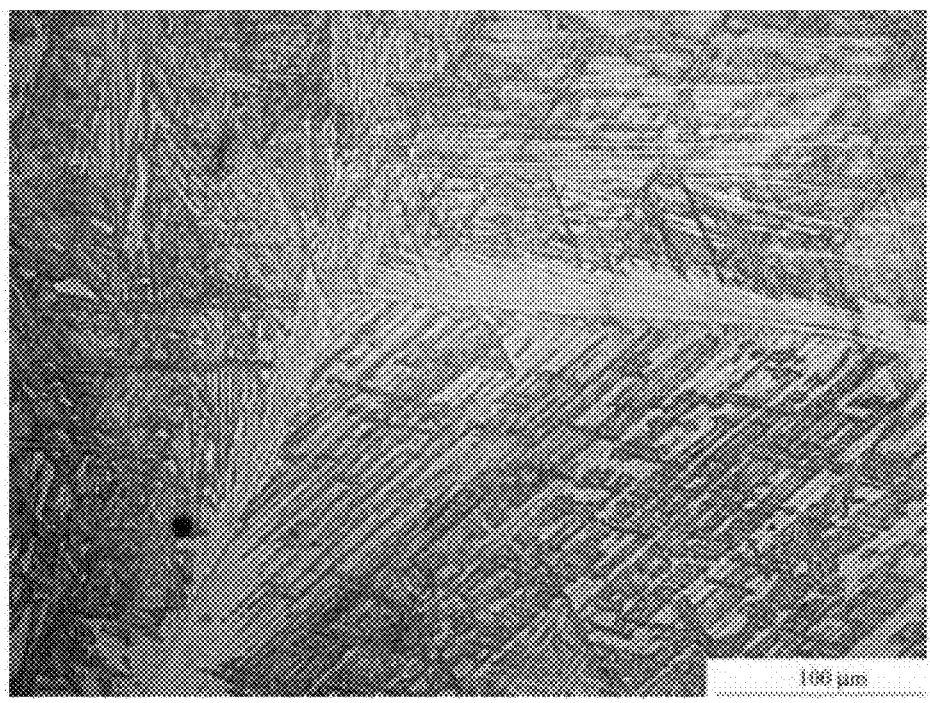
FIG. 6 shows, according to particular exemplary aspects of the present invention, exemplary microstructure of LENS™ fabricated Ti6Al4V parts. Optical micrograph of exemplary inventive Ti6Al4V LENS™ processed part.

FIG. 6 shows exemplary microstructure of LENS™ fabricated Ti6Al4V parts according to aspects of the present invention. Optical micrograph of exemplary inventive Ti6Al4V LENS™ processed part.

Example 2

Cell Growth on LENS Fabricated Macro-Porous Structures

Cell-materials interactions were studied between cp-Ti powder processed LENS parts and OPC1 human osteoblast cells (Winn '99). Cells were plated at a density of $10^5$/cm$^2$ in 100 mm tissue culture plates and cultured in McCoy's 5A medium (with L-glutamine, without phenol red and sodium bicarbonate). 5% fetal calf serum (FCS) and 5% bovine calf serum (BCS), 2.2 gm/liter sodium carbonate, 100 mg/liter streptomycin, 8 g/ml Fungizone (Gibco™ Labortories, Grand Island, N.Y.) were added in the media. LENS processed cp-Ti samples were autoclaved at 121° C. for 45 minutes.

Figure 7:
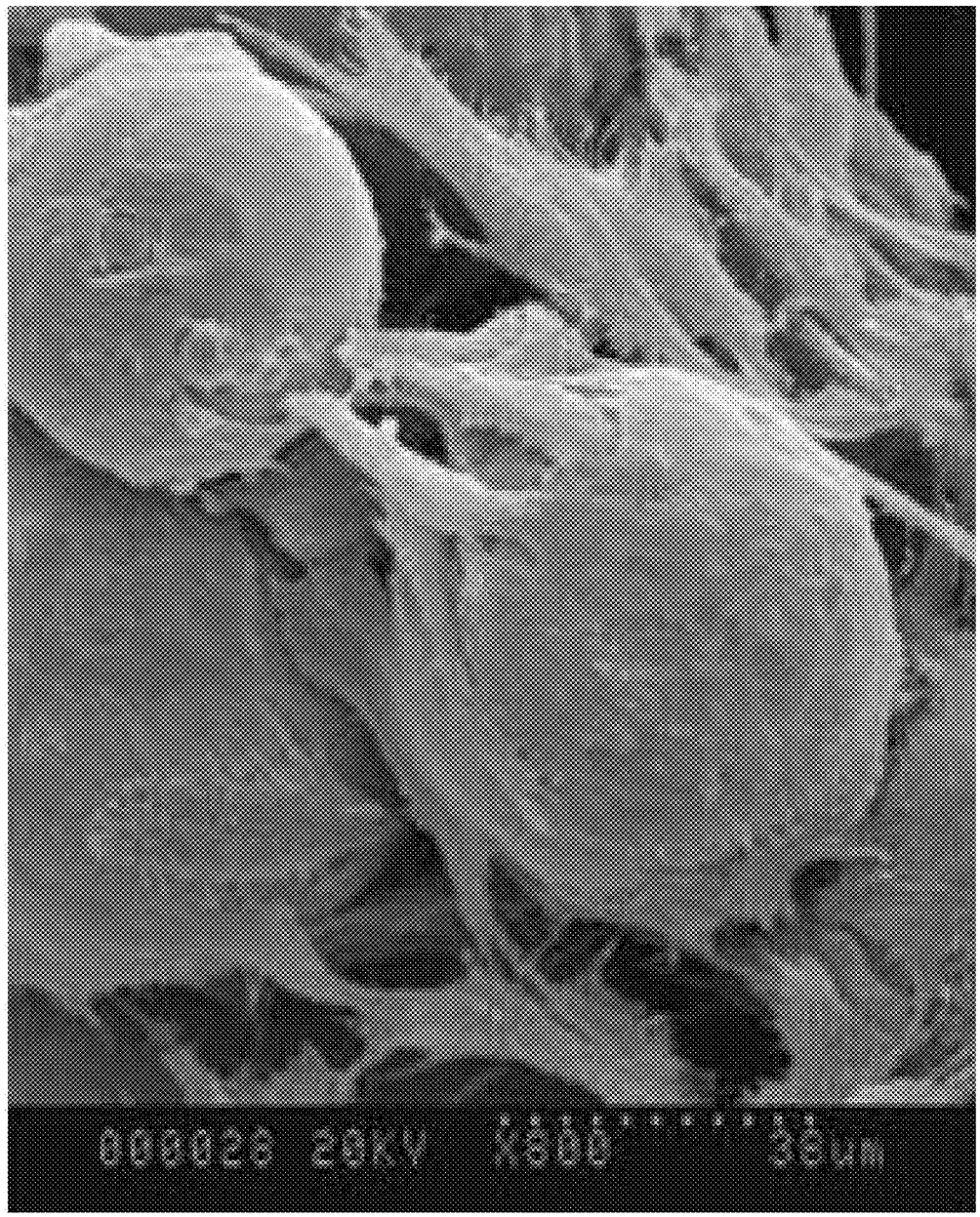
FIG. 7 shows, according to particular exemplary aspects of the present invention, a SEM micrograph of OPC1 on the processed cp-Ti after 3 days in culture. Cells attach tightly on the surface and numerous filopodia-like extensions exist between cell and surface, indicating that the exemplary inventive LENS-processed parts disclosed herein are non-toxic and biocompatible.

FIG. 7 shows a SEM micrograph of OPC1 on the processed cp-Ti after 3 days in culture. It can be seen that cells attach tightly on the surface and numerous filopodia-like extensions exist between cell and surface. This result indicates that exemplary inventive LENS-processed parts are non-toxic and biocompatible.

Example 3

Processing of Nano-Porous TiO$_2$ on Ti and Cell-Materials Interaction

For nano-porous TiO$_2$ materials, commercially pure (99.8% pure) titanium foils of 0.5 mm thickness from Supra Alloys (CA, USA) were used, which was cut into circular pieces of 12 mm diameter. Circular discs were abraded in silicon carbide paper successive grades from 600 to 1200 grit and then cleaned with distilled water in ultrasonic bath. Final polishing was performed in 1 µm alumina powder suspension. Polished titanium foils were ultrasonically rinsed in distilled water followed by isopropyl alcohol prior to anodization. For anodization, a two-electrode electrochemical anodization cell, with a platinum cathode and Ti anode, was used to fabricate the TiO$_2$ nanotube at a constant dc voltage of 20V. Electrolyte solution was made by dissolving sodium fluoride, citric acid, 1(M) sulfuric acid in a ratio so that the final electrolyte components had $F^-$: 0.1 mol/L, $SO_4^{2-}$:1.0 mol/L and citric acid: 0.2 mol/L. The electrolyte pH was adjusted to 4.5 using a NaOH solution. The samples were anodized for three different time periods of 2 h, 4 h and 10 h. All experiments were performed at room temperature.

Figure 8:
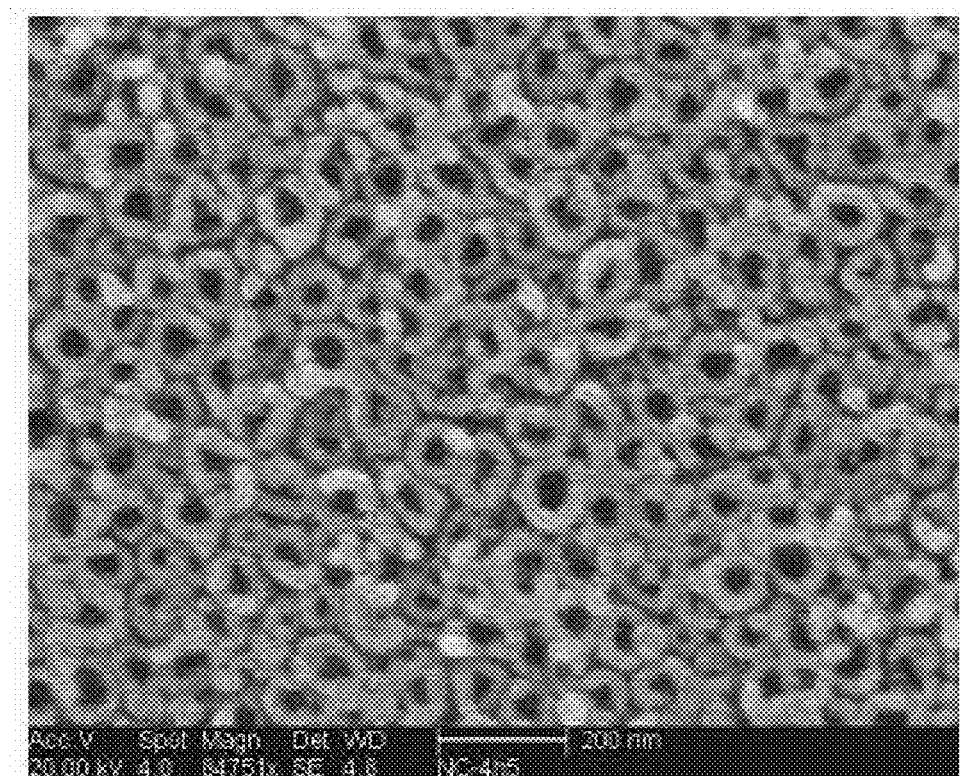
FIG. 8 shows, according to particular exemplary aspects of the present invention, nano-porous TiO2 on a Ti surface; nanoporous surface anodized at 20V for 4 h. Average internal pore diameter was approximately 50 nm with wall thickness ~15 nm.

FIG. 8 shows the nanoporous surface anodized at 20V for 4 h. Average internal pore diameter was approximately 50 nm with wall thickness ~15 nm. Increasing the anodization time to 10h has reduced the average pore diameter to 26 nm. The maximum length of the in situ grown nanotube was ~1 µm. Based on glancing angle x-ray diffraction results, the anodized film formed by electrochemical reactions was amorphous in nature.

Nanotubes are formed by two simultaneous processes—(1) electrochemical etch and (2) chemical dissolution. During electrochemical etching, an initial oxide layer forms due to interaction of $OH^-/O^{-2}$ ions with the Ti-metal ions on the surface. In presence of $F^-$ ions, oxide layers dissolve partially and nanometer sized pits are formed. At the bottom of the pits both chemical dissolution and electrochemical etching takes place forming a thin barrier layer, which in turn increases the electric-field intensity resulting further pore growth. On the surface of the oxide, chemical dissolution removes the top of the shallow pore column, which makes the unanodized metallic region available for electrochemical etching and chemical dissolution. The channels formed in these regions separate pores from each other, giving birth to nanotubes (Cai '05).

To understand cell-materials interactions on anodized surfaces, in vitro biocompatibility assessments were performed. Samples were evaluated for their biological properties using the osteoblast precursor cell line (OPC1) for 3, 7 and 11 days (Winn '99). Cells were plated at a density of $10^5/cm^2$ in 100 mm tissue culture plates and were cultured in McCoy's 5A medium (with L-glutamine, without phenol red and sodium bicarbonate). 5% fetal calf serum (FCS) and 5% bovine calf serum (BCS), 2.2 gm/liter sodium carbonate, 100 mg/liter streptomycin, 8 g/ml Fungizone (Gibco™ Labortories, Grand Island, N.Y.) were added in the media. Anodized nano-porous $TiO_2$ samples were autoclaved at 121° C. for 45 minutes. Cells were seeded from the cultured plate on to the top of the autoclaved samples in other plates. The cell-seeded samples were maintained at 37° C. under an atmosphere of 5% $CO_2$ and 95% air. Culture media were changed every two days for all the plates. All OPC1 cells originated from the same cell line passage and all plates were kept under identical conditions. Cells were cultured for 3, 7 and 11 days to study the cell-materials interaction under SEM. Anodized cell cultured samples were placed in 0.1 M phosphate buffered saline (PBS) and rinsed quickly. Samples were subsequently fixed with 2% paraformaldehyde/2% glutaraldehyde in 0.1 M cacodylate for overnight at 4° C. Following a rinse in 0.1 M PBS, each sample was fixed in 2% osmium tetroxide (OsO4) for two hours at room temperature. The fixed sample was then rinsed three times in 0.1M cacodylate and dehydrated in an ethanol (EtOH) series for 10 minutes each and 100% ethanol three times for 10 minute. Samples were critical point dried using acetone and hexamethyl disilazane (HMDS). Dried samples were mounted in aluminum stubs, gold coated (Technis Hummer, San Jose, Calif.) and observed in SEM.

FIGS. 9A-9B show a comparison of the OPC1 cell attachment on 4 h anodized surface up to 11 days. Excellent cell attachment and proliferation was observed in which microextensions projecting out from the cellular region to the anodized surface could be seen. On the 11-day sample, small calcified nodule as a sign for differentiation is observed.

To further understand the influence of nano-porous structure on cell attachment and growth, anodized surfaces were patterned using a HNA solution (a mixture of hydrofluoric acid, nitric acid and acetic acid) and small circular areas with $TiO_2$ nano-pores were created, stripping the rest of the $TiO_2$ from the surface.

Figures 10A, 10B, 10C:
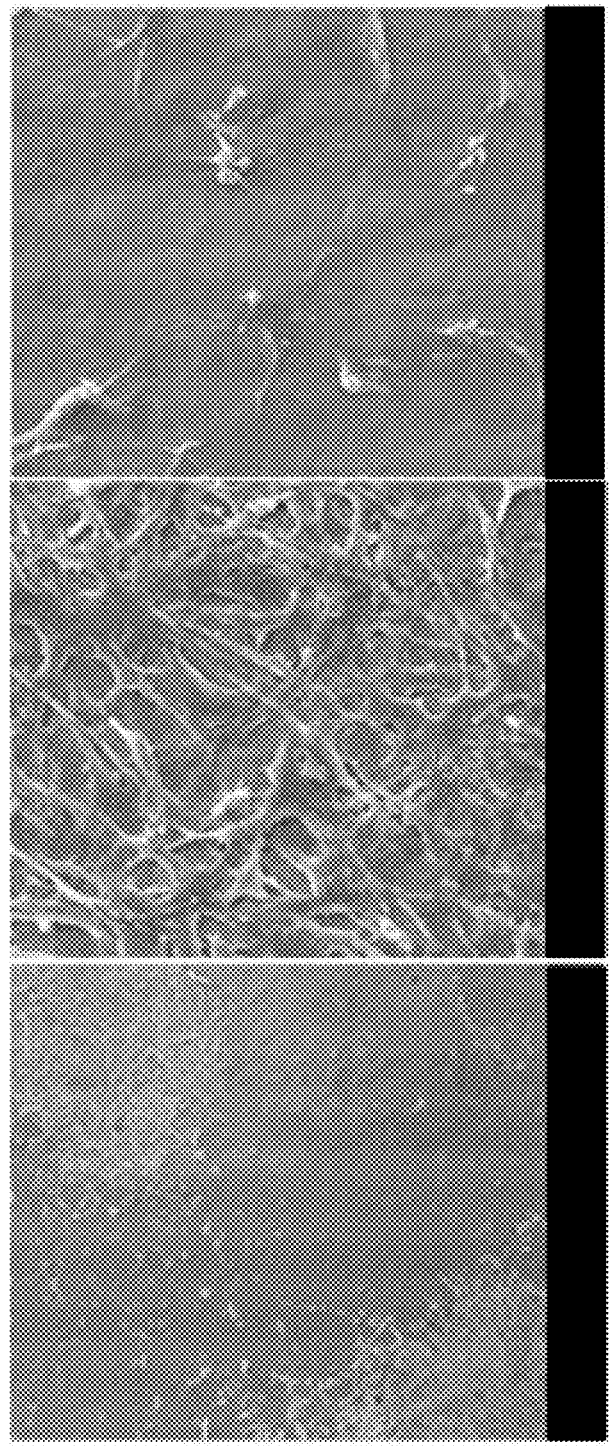
FIGS. 10A-10C show, according to particular exemplary aspects of the present invention, the influence of patterned nano-porous TiO2 surface on human osteoblast cell growth.

FIGS. 10A-10C show a top surface SEM of cell attachment after 5 days. It is clear from the figure that preferential cell attachment took place in regions where nano-porous $TiO_2$ was present. This significant improvement in cell attachment in the nano-porous area over bare Ti surface clearly shows that nano-porous $TiO_2$ improves cell-materials interactions, such as cell-adhesion and growth.

Literature Cited and Incorporated Herein by Reference:

Akasheh F., J. D. Fraser, S. Bose and A. Bandyopadhyay, "Piezoelectric Micromachined Ultrasonic Transducers (pMUTs): Modeling the Influence of Structural Parameters on Device Performance," *IEEE Transactions on Ultrasonics, Ferroelectrics and Frequency Control*, 52 [3], pp. 455-68 (2005).

Ardill J., What is orthopaedics? PhD Thesis. The Department of Orthopaedic Surgery, The Queen's University of Belfast, 1995.

Berndt C C, Haddad G N, Farmer A J D, Gross K A. "Thermal spraying for bioceramic applications", *Mater Forum*; n14: 1990, p 161-173.

Bobyn J D, Glassman A H, Goto H, Krygier J J, Miller J E, Brooks C E. The effect of stem stiffness on femoral bone resorption after canine porous-coated total hip arthroplasty. Clin Orthop Relat Res 1990:196-213.

Brossa F, Cigada A, Chiesa R, Paracchini L, Consonni C., "Adhesion properties of plasma sprayed hydroxyapatite coatings for orthopaedic prostheses", *Biomed Mater Eng*, n3:1993, p 127-136.

Cai Q., M. Paulose, O. M. Varghese, C. A. Grimes, *J. Mater. Res.*, 20, 230-236 (2005).

Cohen J., "Metal implants—Historical background and biological response to implantation", Rubin L. R (ed), *Biomaterials in reconstructive Surgery*, St. Louis, Mo., 46-61 (1979).

Dowson D., "Bio-tribology of natural and replacement synovial joints." In: Mow V. C, Ratcliffe A and Woo S L-Y, editors, *Biomechanics of diarthrodial joints*, vol II. Chap 29. New York: Springer, 305-345 (1992).

Gefen, A., "Computational simulations of stress shielding and bone resorption around existing and computer-designed orthopaedic screws" Med. Biol. Eng. Comput., 2002, 40, 311-322.

Hattiangadi A. and Amit Bandyopadhyay, "Effects of Designed Tubular Porosity on Compressive Strengths of Honeycomb Ceramics," *Journal of Materials Science*, 39 (14): 4575-4586 (2004).

Hoeppner D. W. and V. Chandrasekaran, "Fretting in orthopaedic implants: a review", *Wear*, 173, 189-197 (1994).

Lee C. M., W. F. Ho, C. P. Ju, and J. H. Chern Lin, "Structure and properties of Titanium-25Niobium-xIron alloys", *J. Mater. Sci.: Materials in Medicine*, 13, 695-700 (2002).

LOWERY, G. L., and MCDONOUGH, R. F. (1998): 'The significance of hardware failure in anterior cervical plate fixation. Patients with 2- to 7-year follow-up', Spine, 23, pp. 181-187.

Mow V. C., Soslowsky L. J., Friction, lubrication, and wear of dirthridial joints. In: Basic orthopaedic biomechanics. New York: Raven Press Ltd., 1991:245-92.

Otani T, Whiteside L A. Failure of cementless fixation of the femoral component in total hip arthroplasty. Orthop Clin North Am 1992; 23:335-46.

PILLIAR, R. M., CAMERON, H. U., BINNINGTON, A. G., SZIVEK, J., and MACNAB, I. (1979): 'Bone ingrowth and stress shielding with a porous surface coated fracture fixation plate', J. Biomed. Mater. Res., 13, pp. 799-810.

Pillar R. M., H. U. Cameron and I. Macnab, "Porous Surface Layered Prosthetic Devices," Biomedical Engg. J., 1975, p. 126.

Ryan G., A. Pandit and D. P. Apatsidis, "Fabrication methods of porous metals for use in orthopaedic applications," Biomaterials, Volume 27, Issue 13, pages 2651-70 (2006).

Schumacher H. R., In: Schumacher H R, Klippel J H, Robinson D R, editors. Primer on the Rheumatic Diseases, 9th edn. At-lanta, G A: The Arthritis Foundation, 1988.

Tomita, N., and Kutsuna, T. (1987): 'Experimental studies on the use of a cushioned plate for internal fixation', Int. Orthop., 11, pp. 135-139.

Robertson D M, Pierre L, Chahal R. Preliminary observations of bone ingrowth into porous materials. J Biomed Mater Res 1976; 10: 335-44.

Wang K., "The use of titanium for medical applications in the USA", Mater. Sci. and Eng., A213, 134-137 (1996).

Weber J N, White E W. Carbon-metal graded composites for permanent osseous attachment of non-porous metals. Mater Res Bull 1972; 7(9):1005-16.

Winn S. R., G. Randolph, H. Uludag, S. C. Wong, G. A. Hair and J. O. Hollinger, J. Bone and Mineral Res. 14, (1999).

Example 4

Laser Processed Porous Ti for Biomedical Applications

Example Overview

Musculoskeletal disorders are recognized as among the most significant human health problems that exist today, costing society an estimated $254 billion every year, and afflicting one out of seven Americans. In spite of enormous magnitude of this problem, there is still a lack of bone replacement material that is appropriate for restoring lost structure and function, particularly for load bearing applications. Traditionally, researchers have used available materials that were developed for aerospace or automotive applications, instead of developing new materials tailored specifically for biomedical needs. A typical example is total hip replacements (THR) in which a dense metal is used that had significantly higher density, stiffness and strength than natural bone, which is a porous material. Typical lifetime of a THR is between seven to twelve years and this lifetime has remained almost constant over the past fifty years, even thought significant research and development has gone towards understanding the problem. There are three factors motivating improvements in hip joint prostheses. First, demand for implant will continue to increase due to demographic changes. U. S. Census estimates the total number of people of age 65 and above will increase from 4.9 million to 39.7 million between 2000 and 2010 (1) leading to tremendous increase in the demand for implants and the number of THR has increased from 50,000 worldwide in 1981 to 6000,000 in the US alone in 2001 (1). Second, over the last decade, the age range has been broadened to include older patients who have greater incidence of co-morbidities. Finally, THR are now routinely performed on younger patients, whose implants would be exposed to greater mechanical stresses over time.

The need for adequate mechanical and functional properties coupled with manufacturing flexibility for wide range of metallic implant materials necessitates the use of novel design approaches to fabricate functional implants. Applicants demonstrate herein that application of inventive design concepts in combination with laser processing can significantly increase the processing flexibility of complex shaped metallic implants with three dimensionally interconnected, designed and functionally graded porosities down to 70 vol %, to suit various biomedical applications. Porous Ti samples with biomechanical compatibility were successfully fabricated in the porosity range from 25 to 70 vol % by controlling Laser Engineered Net Shaping (LENS™) process parameters. Young's modulus and compressive strength of these porous Ti samples having the porosity in the range of 35-42% are close to those of human cortical bone.

A summary of the physical and mechanical properties of various implant materials in comparison to natural bone is shown in TABLE 1:

TABLE 1

Mechanical properties of various biomaterials used in THR (adapted from [27, 42, 45-47]).

| Material | Density (g/cc) | Compressive Strength (MPa) | Elastic Modulus (GPa) | Toughness, MPa · m$^{1/2}$ | Comments |
|---|---|---|---|---|---|
| Natural Bone | 1.8-2.1 | 130-180 | 3-20 | 3-6 | |
| Ti & Ti alloys | 4.4-4.5 | 590-1117 | 55-117 | 55-115 | High strength |
| Co—Cr—Mo alloys | 8.3-9.2 | 450-1896 | 200-253 | 100 | and elastic |
| Stainless Steels | 7.9-81 | 170-310 | 189-205 | 50-200 | modulus |
| Magnesium | 3.1 | 65-100 | 41-45 | 15-40 | compared to nature bone leading to 'stress-shielding'. |
| High density polyethylene (HDPE) | 0.94-0.96 | 25 | 1-2 | *** | Relatively low strength and |
| Ultrahigh molecular weight polyethylene (UHMWPE) | 0.41-0.49 | 28 | 1 | 20 | modulus limits the use of polymers for |
| Polytetrafluoroethylene (PTFE) | 2.1-2.3 | 11.7 | 0.4 | *** | load bearing applications. |
| Polymethylmethacrylate (PMMA) | 1.16 | 144 | 4.5 | 1.5 | |
| Zirconia | 6.1 | 2000 | 220 | 9 (MNm$^{-3/2}$) | Inherent |
| Alumina | 3.98 | 4000-5000 | 380-420 | 3-5 | brittleness and |

TABLE 1-continued

Mechanical properties of various biomaterials
used in THR (adapted from [27, 42, 45-47]).

| Material | Density (g/cc) | Compressive Strength (MPa) | Elastic Modulus (GPa) | Toughness, MPa · m$^{1/2}$ | Comments |
|---|---|---|---|---|---|
| Bioglass | 2.7 | 1000 | 75 | *** | low fracture toughness. |
| Hydroxyapatite (HAP) | 3.1 | 600 | 73-117 | 0.7 | |
| AW Glass-Ceramic | *** | 1080 | 118 | 1.9-2 | |

The composition of metallic implant materials is significantly different from that of natural bone. However, the necessary toughness and fatigue resistance for load-bearing implants can only be realized in metals. As a result, use of metallic materials for implants in load-bearing application is unavoidable. Among various metallic biomaterials, Ti and its alloys have been recognized as desirable materials, for bone implants, because of their excellent corrosion resistance, biocompatibility, mechanical properties and high strength-to-weight ratio (2-6).

The first major problem concerning these metallic implants in orthopedic surgery is the mismatch of Young's modulus between bone (10-30 GPa) and metallic materials (110 GPa for Ti). Due to this mechanical property mismatch, bone is insufficiently loaded and becomes stress shielded, leading to bone resorption. The mismatch of Young's moduli has been identified as a major reason for implant loosening following stress shielding of bone (7-9). Many investigators have shown that the stress-shielding retards bone remodeling and healing, which results in increased porosity in surrounding bone (10, 11).

The second problem with metallic implants lies in the interfacial bond between the tissue and the implant, and weak interfacial bond due to stiffer replacement materials reduces the lifetime of the implant. An ideal implant should have the same chemistry as natural bone, have similar mechanical properties, and should bond well with human tissue.

An alternative to overcome 'stress-shielding' and weak interfacial bond between the tissue and the implant, is the use of porous materials. Use of porous materials in implants can reduce the stiffness mismatches and achieve stable long-term fixation due to full bone ingrowth. The rough surface morphology of porous implant promotes bone ingrowth into the pores and provides not only anchorage for biological fixation but also a system which enables stresses to be transferred from the implant to the bone (12) leading to long-term stability (13, 14). To achieve tissue ingrowth and to attain better mechanical interlock between implants and bone, metallic implants formed with porous surface coatings have been developed. Also, mechanical properties of porous materials can be altered and optimized by controlling porosity, pore size and shape as well as pore distribution to suit the natural bone. A number of approaches to the fabrication of porous-surface implants have been reported, including Ti powder or fibers sintering, plasma spray coating, and the void-metal composite method (13, 15-22). However, porous surface implants suffer with loss of physical properties (e.g., fatigue strength) due to stress concentrations at the porous interface, and changes in microstructure and surface contamination from the high-temperature sintering process (15, 23, 24).

Commercially pure Ti (15, 25) has been used to create fully porous implants, using particles ranging in size from 50 mm to 1 mm. Wen et al. have successfully fabricated Ti foams with a porosity of 78% using a powder metallurgical process (26). These foams have unique open-cellular structure and achieve low Young's modulus (5.3 GPa), but the compressive strength is not sufficient for the human cortical bone. Moreover, the limitation of the powder sintering approach is that pore size and shape are dictated by the powder size and shape and are difficult to control. Sintered metal powders are often very brittle and are prone to crack propagation at low stresses. Under fatigue conditions, cracks are likely to initiate at the sintered necks of individual powder particles. Also, the pore size, volume fraction, morphology and distribution throughout the sample thickness and the inter particle neck size have a major impact on the mechanical properties. Current techniques that use foaming agents, either in solid state sintering processes or in molten metal techniques have inherent limitations such as contamination, presence of impurity phases, limited and predetermined part geometries, limited control over the size, shape, and distribution of the porosity. A recent review (27) on fabrication methods of porous metals indicate that there is a significant demand for fabrication methods which can ensure uniform pore size, shape and distribution, and high levels of purity for metals in biomedical applications.

Complex shaped implants can not be fabricated using these traditional methods and the properties of the samples made are mechanically inadequate. The need for adequate mechanical and functional properties coupled with manufacturing flexibility for wide range of metallic implant materials, necessitates the use of novel design approaches to fabricate functional implants. The design approach should be able to fabricate functional implants with designed macro and micro porous structures to achieve desired mechanical and functional performance. This complex design approach to build functional implants can be implemented using layered manufacturing processes, generally known as solid freeform fabrication. Over the past few years, direct fabrication of metallic components using the solid freeform fabrication route has been shown to be a viable and promising near-net shape manufacturing technology. One such rapidly developing process is the Laser Engineered Net Shaping (LENS™) process, which uses metal powders to create functional parts that can be used in very demanding applications. This solid freeform approach to fabricate parts in layer-by-layer fashion allows the user to produce parts with features that cannot be readily reproduced by other manufacturing methods. Moreover, this technique has advantage of fabricating parts directly from a CAD file and allows us to control the shape, size and internal architecture of porous structures. Appropriate combination of processing parameters usually result in solidification rates of ~$10^3$ to $10^5$ K/sec in LENS™ processing leading to formation of fine-grained chemically homogeneous microstructures with good mechanical properties. Much of the previous work using LENS™ has been focused on alloy development (28-31), gradient structures (32-35), net shape manufacturing (36, 37), coatings (38-40), etc. Applicants have used this technique to fabricate porous implants with maximum functionality and with mechanical properties matching those of natural bone.

Figure 12A:
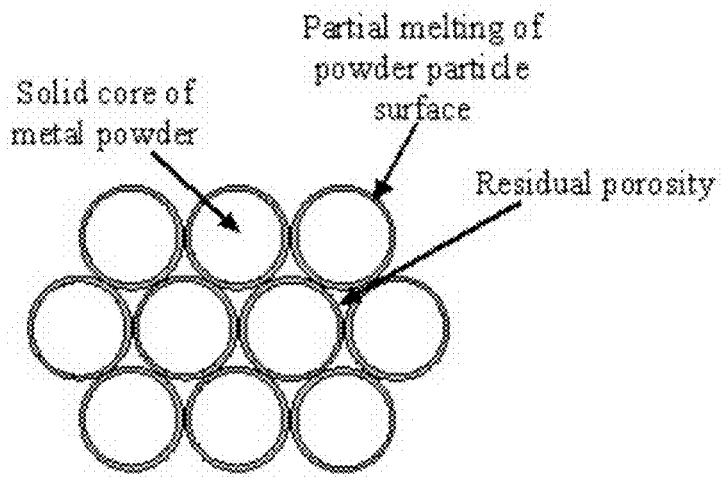
FIGS. 12A-12C show, according to particular exemplary aspects of the present invention, an inventive conceptual design to fabricate complex shaped implants with tailored and functionally graded porosity.
Figure 12B:
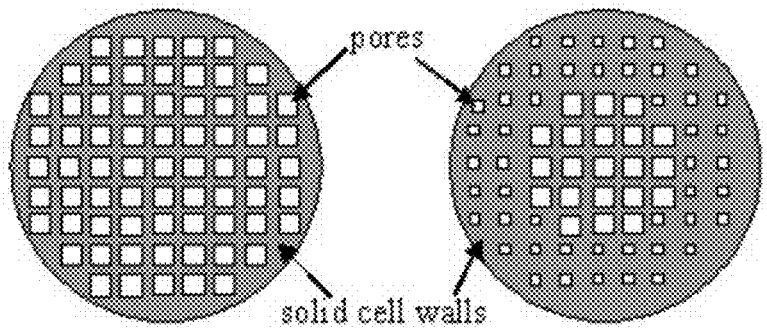
Figure 12C:
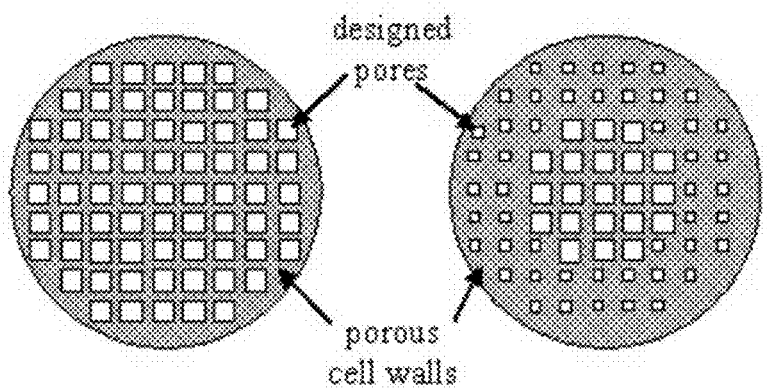

The inventive design philosophy to fabricate complex shaped implants with designed and functionally graded porosity, to suit natural bone, using LENS™ is schematically shown in FIGS. 12A-12C. In exemplary approach shown in FIG. 12A, complete melting of the metal powder is avoided by using appropriately low laser power which would partially melt the metal powder surface that is fed to the laser beam. These surface melted powders join together due to the presence of liquid metal at the particle interfaces, leaving some interparticle residual porosity. The particle bonding in this case is similar to liquid phase sintering as against solid state sintering in powder metallurgical route (25). Therefore, the inherent brittleness associated with solid state sintered metal powders can be eliminated as the necks between the powder particles in this approach have high strength due to fine, homogeneous cast structure. By changing the scan speed, the interaction time between the powder particles and the laser beam can be varied resulting in more porous or dense structures. Similarly, powder feed rate has a strong influence on the laser energy density on the powder particles due to volume changes associated with it in the laser-material interaction zone.

Approach B (FIG. 12B) can be used to fabricate structures with different porosity parameters/internal architecture with designed gradient across the part. The porosity parameters and gradient can be tailored by optimizing the distance between two successive metal roads (laser scans) and the thickness of each metal layer. Moreover, by changing the deposition angles of laser scans for each layer, the pores can be oriented layer by layer, leading to three-dimensionally interconnected porosity. The walls in these structures are solid in nature and provide better strength to the structure at relatively low bulk densities. Finally, these solid walls can also be made porous by combining the above two approaches shown in FIG. 12C. The objective of present investigation is to fabricate porous Ti structures using LENS™, and control the mechanical properties to match with the properties of human bone for biomedical applications. In the present implementations, systematic experiments were conducted to understand the influence of laser processing parameters on the porosity and mechanical properties of porous Ti.

Figure 13:
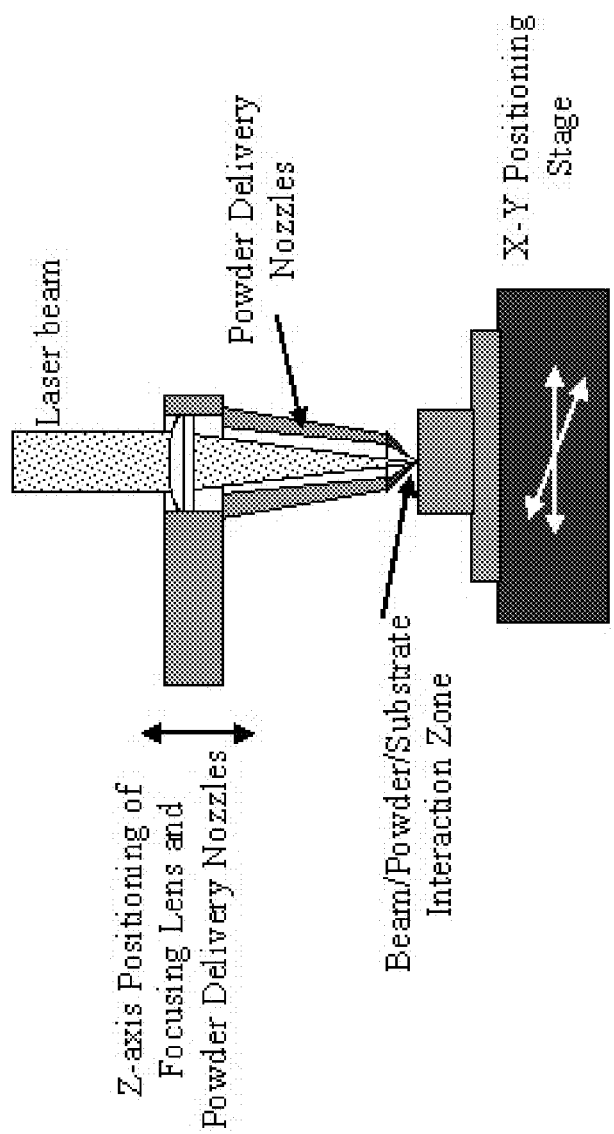
FIG. 13 shows, according to particular exemplary aspects of the present invention, a schematic representation of LENS™ process.

Experimental:

Schematic representation of the LENS™ process is shown in FIG. 13. The process uses Nd:YAG laser, up to 2 kW, power focused onto a metal substrate to create a molten metal pool on the substrate. Metal powder is then injected into the metal pool which melts and solidifies. The substrate is then scanned relative to the deposition head to write line of the metal with a finite width and thickness. Rastering of the part back and forth to create a pattern and fill material in desired area allows a layer of material to be deposited. Finally, this procedure is repeated many times until the entire object represented in the three-dimensional CAD model is produced on the substrate, which is a solid or tailored porosity object.

Figure 1C:
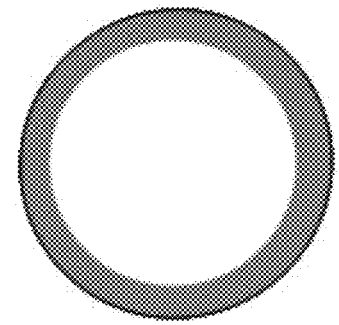
Figure 1D:
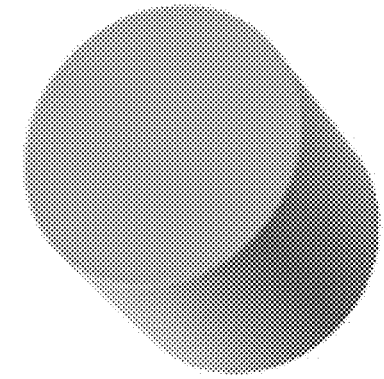

Commercially pure (CP) titanium powder (Advanced Specialty Metals, Inc. NH) with particle size between 50-150 μm was used in this Example. Porous samples were fabricated on a substrate of rolled Ti plates with 3 mm thickness. The specimens and the substrates used in this study were loosely bonded in order to remove the specimens easily. This is achieved by using high powder feeding rate or low laser power during initial 2-3 layers. A LENS™ unit with 500 W Nd-YAG laser system was used to fabricate the porous Ti samples. The samples were fabricated in a controlled atmosphere with $O_2$ content less than 10 ppm to limit oxidation of the titanium during processing. The main process parameters varied were laser power, scan speed, powder feed rate and hatch distance (distance between two successive metal roads or laser scans). Initial optimization studies showed that a laser power in the range of 400-450 W would result complete melting of Ti powder leading to dense deposit on the substrate. Therefore, laser powers of 250 and 300 W were chosen to partially melt the metal powder during deposition process to create porous structures. By changing the scan speed, at constant laser power and powder feed rate, the interaction time between the powder particles and the laser beam is varied resulting in variation in the porosity of the structures. For particular combination of laser power and powder feed rate, slower scan speeds would lead to more interaction time between the material and laser beam leading to high amount of melting and denser deposits. In this work scan speeds of 5, 10, 15 and 18 mm/s were used to fabricate structures with varying porosity. Similarly, by changing the powder feed rate to the beam-material interaction zone the energy density on the material was varied. Low energy density at high feed rates would partially melt the metal particles leading to interparticle residual porosity. Applicants have used powder feed rates of 18, 23, 28 and 38 g/min in our work. Also, the distance between two successive metal roads or laser scans was varied between 0.762 to 9.52 mm to tailor the pore size and distribution as shown in FIG. 1C. A series of samples, following two different design philosophies, have been produced using different process parameters as shown in TABLE 2:

TABLE 2

Processing parameters used to fabricate porous Ti samples.

| Parameter | Approach A | Approach C |
| --- | --- | --- |
| Laser Power, W | 250, 300 | 250, 300 |
| Scan Speed, mm/s | 5, 10, 15 | 18 |
| Powder Feed Rate, g/min | 18, 23 | 28, 38 |
| Hatch Distance, mm | 0.762, 1.27 | 1.27 |
| Z-increment, mm | 0.127-0.508 | 0.177-0.228 |

The Z-increment was also varied to suit the layer build height for each processing parameter combination. This will ensure a constant standoff distance between the substrate and laser head. Cylindrical samples of 12 mm and 6 mm diameter were fabricated for microstructural and mechanical property evaluation, respectively. The density of the samples was determined by measuring the physical dimensions and mass of the samples. The microstructures of the samples were examined using both optical microscopy and scanning electron microscopy (SEM) to evaluate the pore interconnectivity. Quantitative image analysis was carried out on 10-12 optical microstructures to determine the average pore size and its distribution. The diameter of isolated pores (diameter of a circle having same area as the irregular pore) was calculated as:

$$\sqrt{\frac{4 \times \text{area of the pore}}{\pi}}.$$

Three samples from each density of as-processed samples were compression tested in screw driven universal testing machine at a strain rate of $10^{-3}$ s$^{-1}$. The compression platens were coated with polytetrafluoroethylene (PTFE) lubricant to reduce friction between the cylindrical compression specimens and the tools, which were nominally 9 mm in length and 6 mm in diameter. The modulus of porous Ti samples was determined from the linear region of the nominal stress-strain response. The compressive strength values of samples were determined from the first peak in the stress-strain curve. Vickers microhardness measurements (Leco, M-400G3) were also made on the as-fabricated porous Ti samples using 100 g load for 15 s and average value of 10 measurements on each sample was reported.

Figure 14A:
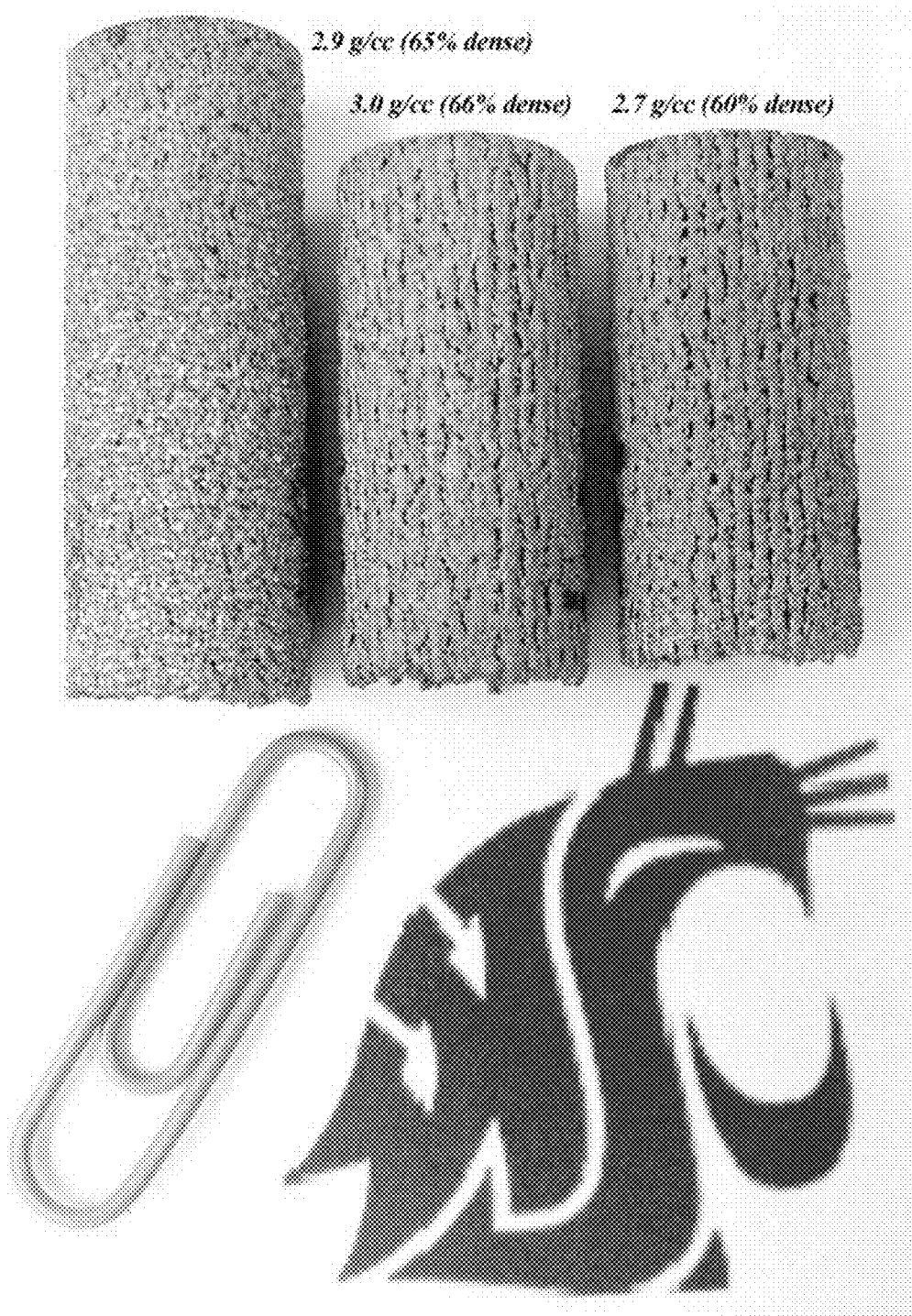
FIG. 14 shows, according to particular exemplary aspects of the present invention, a typical CP titanium structures fabricated using different design procedures (a) samples fabricated using approach A: 250 W, 5-15 mm/s scan speed, 0.762 mm hatch distance, 18 g/min powder feed rate (b) samples with designed porosity with porous walls via approach C: 250 W, 1.27 mm hatch distance, 28-38 g/min powder feed rate, 18 mm/s scan speed.
Figure 14B:
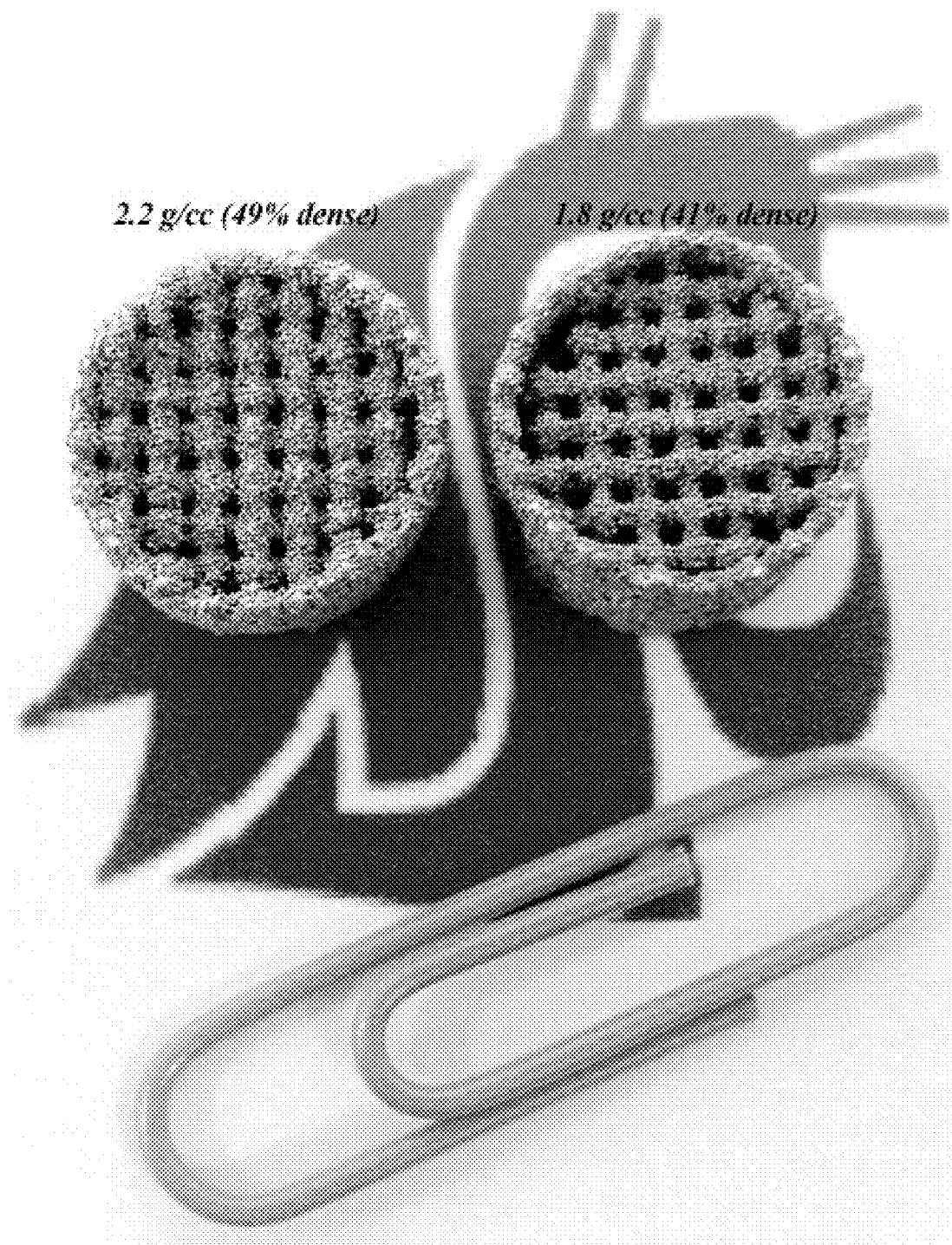

Results and Discussion:

Porous Ti samples fabricated using different design procedures are shown in FIG. 14. The bulk density of these samples varied depending on the LENS™ processing parameters. Samples processed under approach A, at 250 W, 0.762 mm hatch distance and 18 g/min powder feed rate showed porosity, which was open to the sample surface (FIG. 14A). As the scan speed increased to 18 mm/s along with the powder feed rate to either 28 or 38 g/min the samples showed regularly arranged pores interconnected three-dimensionally (FIG. 14B).

Figure 15:
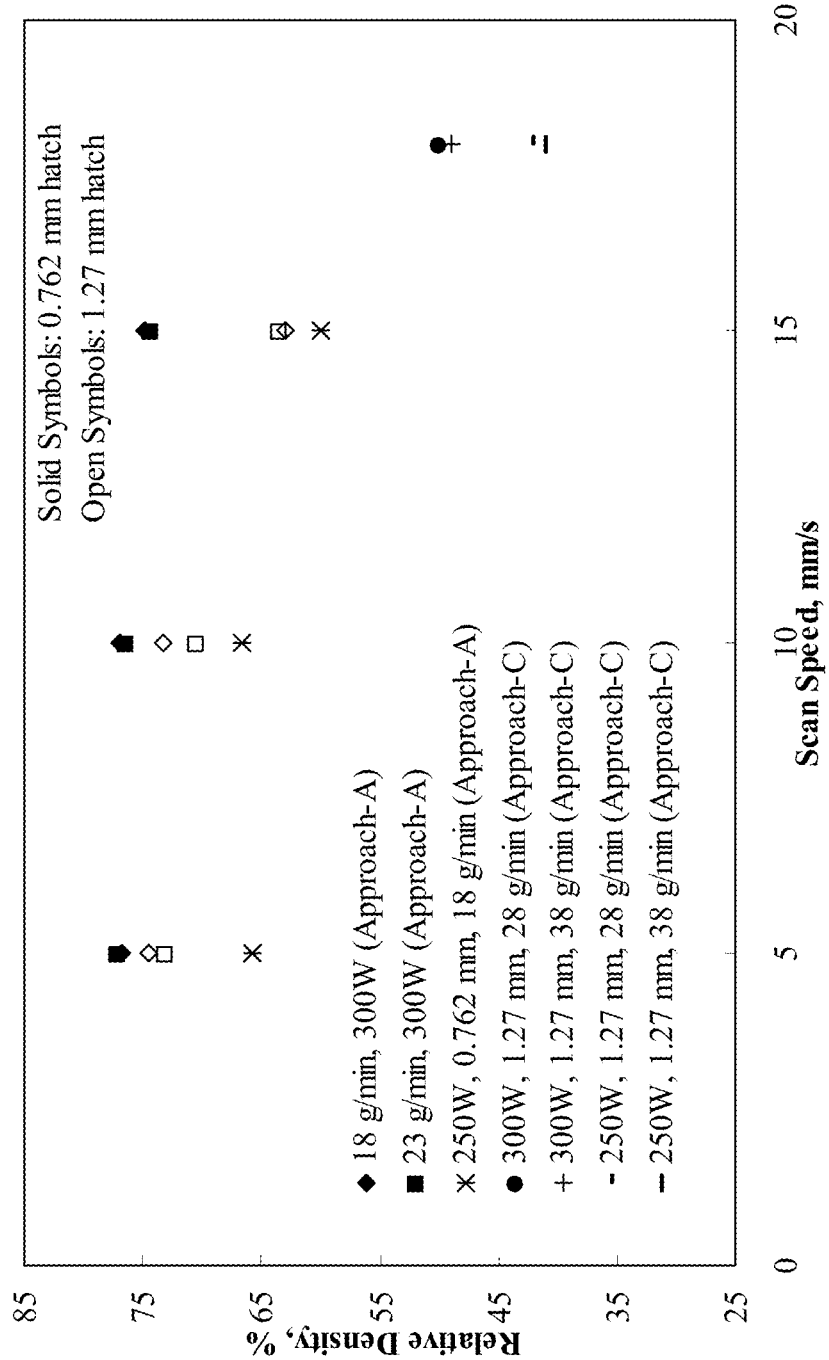
FIG. 15 shows, according to particular exemplary aspects of the present invention, relative density of LENS™ processed porous Ti samples.
Figure 16B:
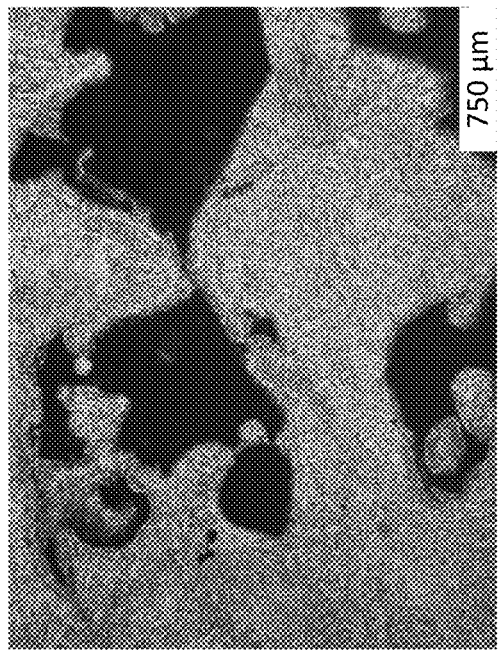
FIGS. 16A-16D show, according to particular exemplary aspects of the present invention, typical optical microstructures of porous Ti samples showing variations in pore size, shape and pore connectivity (a) 300 W, 5 mm/s, 18 g/min, 0.762 mm (b) 300 W, 5 mm/s, 23 g/min, 0.762 mm, (c) 300 W, 15 mm/s, 23 g/min, 1.27 mm, and (d) 250 W, 15 mm/s, 18 g/min, 0.762 mm, respectively.
Figure 16D:
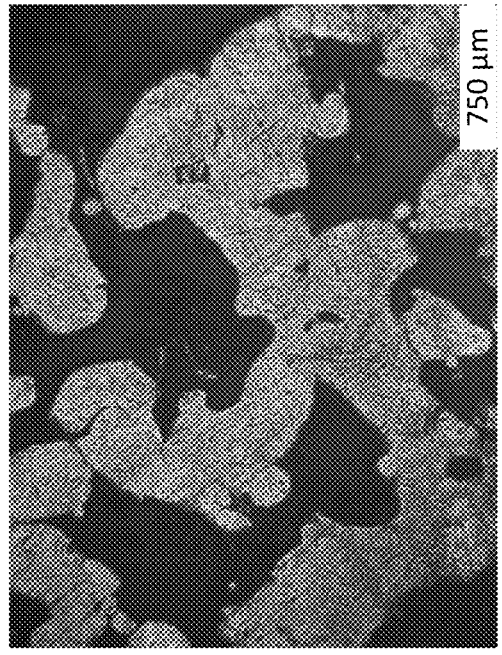
Figure 16A:
Figure 16C:
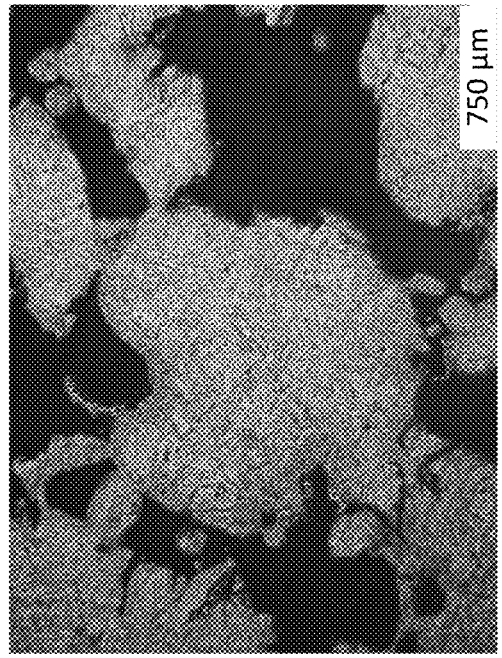

The density of porous Ti samples was measured from the weight and apparent volume of the sample. Influence of various processing parameters and design approach on the density of LENS™ processed porous Ti samples is shown in FIG. 15. The relative density of the samples varied from 30-77% depending on the processing parameters and design approach. The density of laser processed Ti samples, using approach A, decreased with increasing scanning speed. Similarly, increasing the powder feed rate or decreasing the laser power increased the porosity of the samples. On the other hand, higher hatch distance resulted in highly porous samples. At constant laser power and powder feed rate, increasing the scan speed results in decreased interaction between the powder and laser. Therefore, the instantaneous laser energy absorbed by the powder also decreases with increasing scan speed leading to relatively less amount of liquid phase around the metal powders. As a result, the particle rearrangement, which is considered responsible for high sintered density in liquid phase sintering, will be less in this case leading to high porosity in the samples processed at high scanning speed. This explanation holds good as the laser power is decreased—other parameters being held constant. On the other hand, increasing the powder feed rate to the melt pool on the substrate results in more volume of powder in the laser-materials interaction zone. Under this condition it is reasonable to expect a decrease in the laser energy density on the powders leading to partial melting of the powder and consequent high porosity in the samples. Increase in the porosity level at higher hatch distance is obvious, as the powder will be deposited at wider spacing between successive scans. The density of these porous Ti samples processed under approach A is in the range of 2.7-3.5 g/cc which is slightly higher than the density of nature bone (1.8-2.1 g/cc). Density of CP Ti structures made using approach C was found to be in the range of 1.8-2.2 g/cc. It is important to note that these density values match well with the density of natural bone.

A microstructural study was carried out on transverse and longitudinal sections of porous samples to evaluate the pore interconnectivity, pore size and shape. The pores were found to be irregular in shape in all the samples processed under various processing parameters, as shown in FIGS. 16A-16D. The pore size and their connectivity was low in the samples fabricated at 300 W, 18 g/min powder feed rate and hatch distance of 0.762 mm under various scan speeds. This is attributed to the relatively high energy density and high amount of liquid phase under these process parameter combinations. However, pore size and interconnectivity were increased by increasing the hatch distance to 1.27 mm under identical energy density. This is in line with the anticipated increase in the space between successive laser scans. Also, the overlap region between the successive scan will be reduced by increasing the hatch distance. Hence, the re-melted region in the first scan (road), due to second scan, will also be low resulting in higher porosity. At low hatch distance, due to high amount of re-melting of existing solidified road by the next scans results in more densification in this region. At 0.762 mm hatch distance considerable increase in the pore interconnectivity was achieved by increasing the powder feed rate from 18 g/min to 23 g/min, as shown in FIG. 5b. Highly interconnected porosity coupled with low density was observed in the samples processed at low laser power, high hatch distance, high powder feed rate and high scan speed (FIGS. 5c, d). The pore connectivity was found to be different in longitudinal and transverse sections of the samples.

Figure 17A:
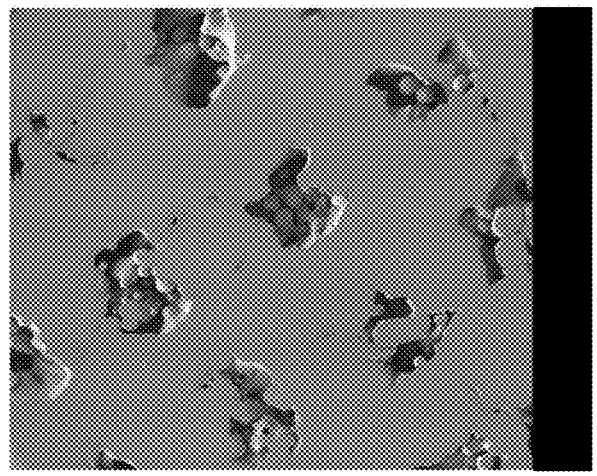
FIGS. 17A-17C show, according to particular exemplary aspects of the present invention, Micrographs illustrating pore connectivity (a) transverse section, 300 W, 23 g/min, 10 mm/s, 1.27 mm (b) same as (a) longitudinal section, and (c) 250 W, 28 g/min, 18 mm/s, 1.27 mm, respectively.
Figure 17B:
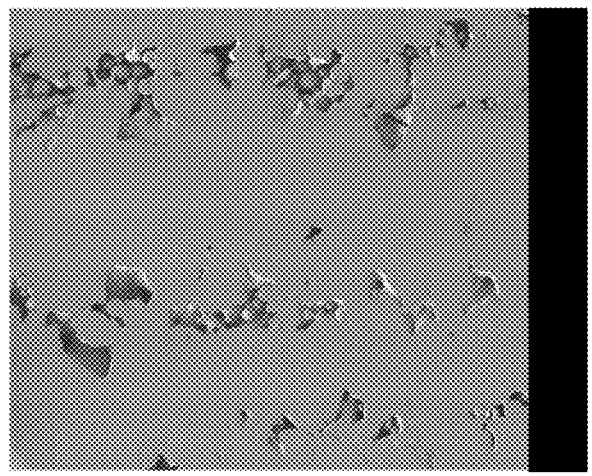
Figure 17C:
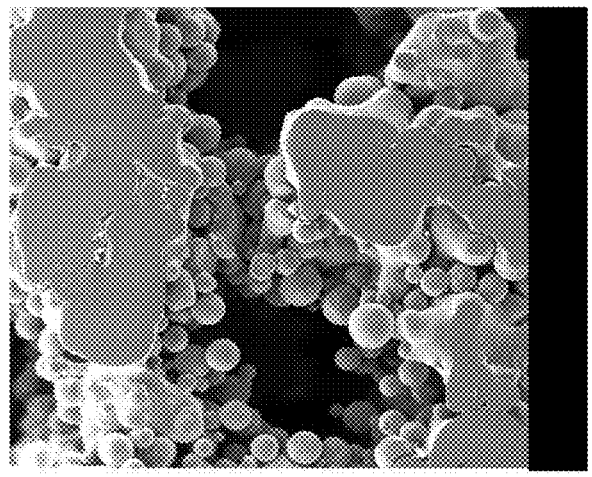

FIGS. 17A-17C show typical transverse and longitudinal section microstructures of samples processed at different processing conditions. In general, the pore connectivity was more in longitudinal direction compared to the connectivity in the transverse direction. This is more clearly seen in the case of samples processed at low hatch distance, low powder feed rate, low scan speed and high laser powers. However, the pore connectivity was uniform in both directions in the low density samples (FIG. 17C). The mean pore diameter of the samples was in the range of 60-700±20 μm. Although relative density decreased with increase in the scan speed or powder feed rate or decrease in the laser power, qualitatively no significant change in the pore diameter was noted. Hatch distance was found to have strong influence on pore diameter and the mean pore diameter increased with increase in the hatch distance for all processing parameter combinations. The total porosity is in the range of 23-70 vol %, and the open porosity is >90 vol % in low density samples, suggesting that most pores are interconnected three-dimensionally in the porous structures processed using approach A and C. Closed pores were observed only in the samples with porosities less than 25%. It is important to note that the present samples with the porosities greater than 25 vol % are promising for biomedical applications, since the optimal porosity of implant materials for ingrowths of new-bone tissues is in the range of 20-50 vol % (41).

Figure 18A:
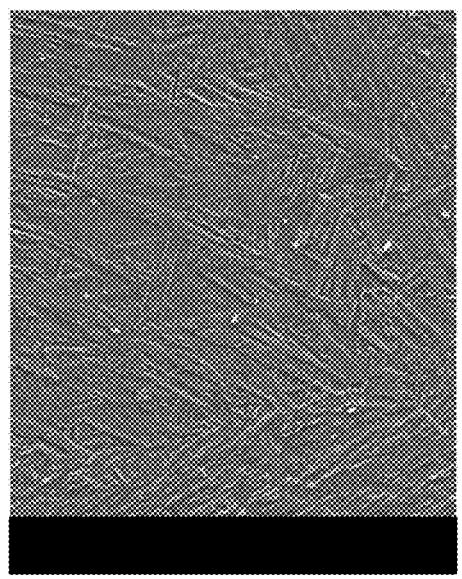
FIGS. 18A-18B show, according to particular exemplary aspects of the present invention, (a) typical microstructure of laser processed porous Ti and (b) microhardness of porous Ti samples fabricated under various processing conditions, respectively.
Figure 18B:
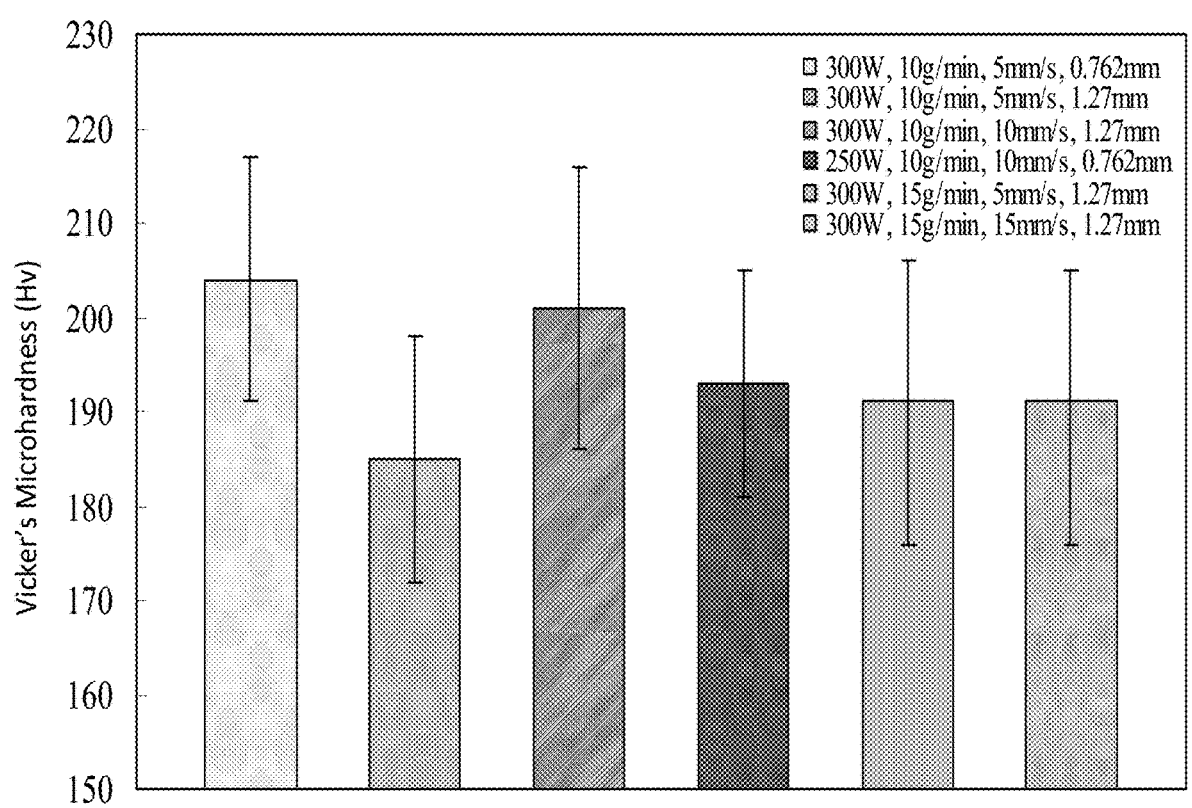

Typical matrix microstructure of laser processed CP Ti samples is shown in FIG. 18A. The microstructure contained acicular α and the structure did not change with laser processing parameters. This observation is supported by the microhardness measurements carried out on various samples. The variation in the hardness of samples fabricated under various processing conditions is within the standard deviation FIG. 18B). The average hardness of these Ti samples was found to be 194±14 Hv, which is higher than the hardness of conventionally processed CP Ti (145 Hv). The high hardness of laser processed material is attributed to the high solidification rates of laser processing leading to formation of finer and acicular α at room temperature. Identical microstructure of various laser processed titanium structures indicate that the inherent biocompatibility of CP Ti is retained in all structures with varying porosity.

Figure 19:
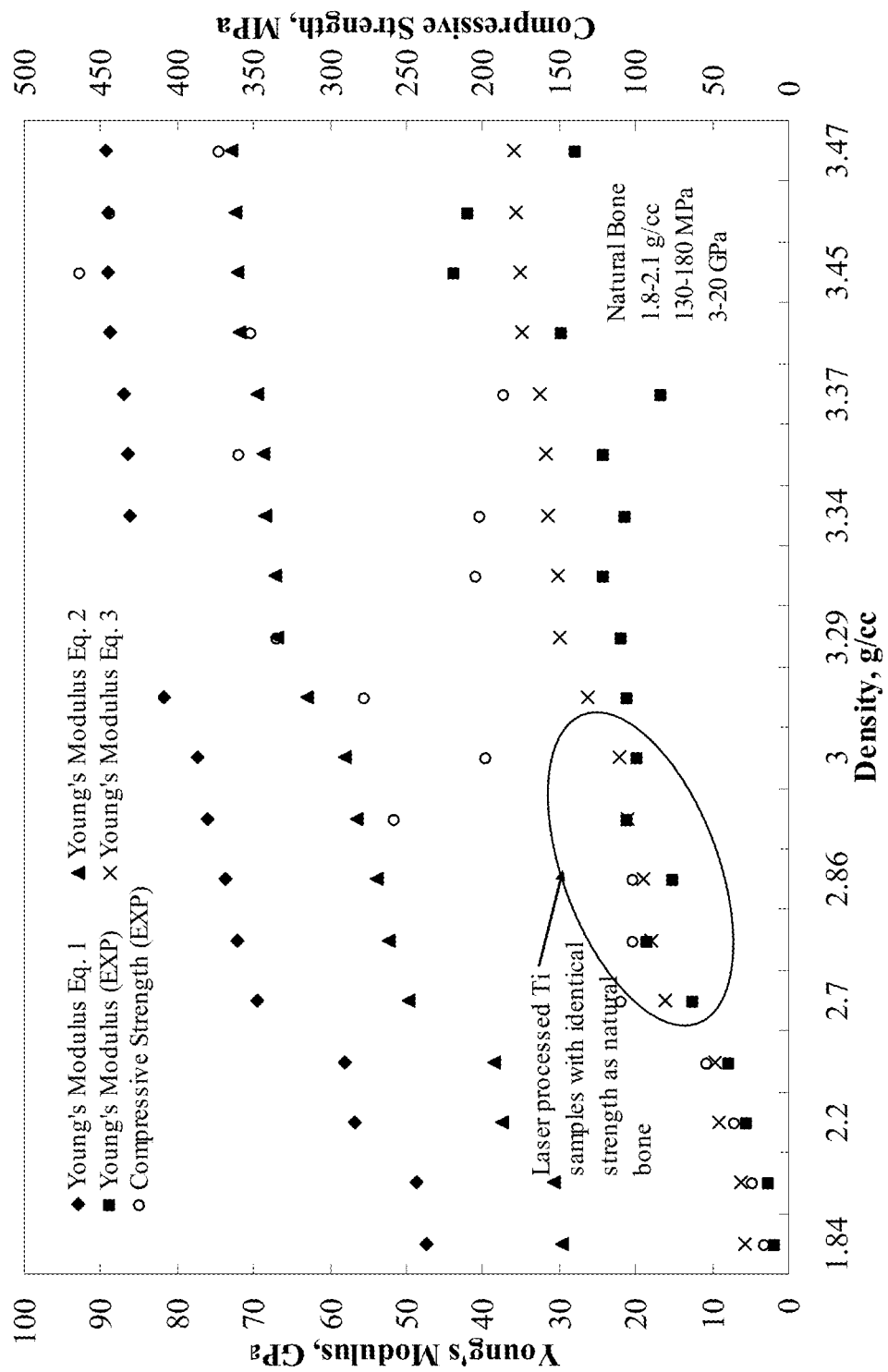
FIG. 19 shows, according to particular exemplary aspects of the present invention, Mechanical properties of laser processed porous Ti samples. Properties of samples with density in the range of 2.6-2.9 g/cc (porosities 35-42 vol %) is almost the same as that of human cortical bones.

The compression strength and Young's modulus of porous Ti samples are shown in FIG. 19. Young's modulus increased linearly with increasing density of the samples. The experimental data indicate that the modulus of laser processed Ti samples can be tailored in the range of 2 and 50 GPa by changing the LENS™ process parameters. The Young's modulus of the samples having density in the range of 2.6-2.9 g/cc (porosities 35-42 vol %) is almost the same as that of human cortical bones. As shown in FIG. 19, these porous Ti samples have compressive strengths in the range of 16-463 MPa, which cover the strength of bone (130-180 MPa) (42). It was reported that the measurements of mechanical properties were limited in the porosity range from 0 to 40 vol %, because the strength of compacts with porosity higher than 40 vol % becomes almost 0 MPa (25, 43, 44). However, our results demonstrate that it is possible to fabricate porous Ti samples with porosity greater than 40% by changing the laser processing parameters, which have measurable mechanical properties. The density (2.6-2.9 g/cc) of porous Ti samples with matching mechanical properties with natural bone is higher than the density of natural bone (1.8-2.1 g/cc) due to inherent high density of titanium. However, porous Ti with density in the range of 1.8-2.2 g/cc, fabricated under approach C, showed considerably lower mechanical properties than natural bone. The strength of these samples with matching density can be increased by post-sintering operation which increases the interparticle bonding and hence the strength. For porous elastic materials, the relationship between elasticity modulus and porosity has been widely investigated. An attempt has been made here to evaluate the suitability of three different relationships in estimating the Young's modulus of laser processed porous Ti samples.

Based on linear rule of mixtures [48]:

$$E = v E_p + (1-v) E_m \qquad \text{Equation 1}$$

Based on Mori-Tanaka theory [49], assuming spherical void shapes, and neglecting the effect of changing Poisson's ratio, it gives the following approximate expression for elasticity modulus as a function of porosity:

$$E = \frac{E_m (1-v)}{(1+v)} \qquad \text{Equation 2}$$

Nielsen's relationship [50]:

$$E = E_m \frac{(1-v)^2}{1 + \left(\frac{1}{\rho} - 1\right) v} \qquad \text{Equation 3}$$

where: E=Young's modulus of porous material.
$E_m$=Young's modulus of pore free/fully dense material (116 GPa for Ti).
v=Volume fraction of porosity.
$\rho$=Geometry factor based on pore shape.
(In the present work geometry factor (0.2) was taken as the roundness of the pores computed as:

$$\left(\frac{4 \times \pi \times \text{Area}}{\text{Perimeter}^2}\right).$$

Estimated modulus values using above three equations are shown in FIG. 8, along with the experimental values. The modulus values calculated using Eq. 1 shows the upper limit of modulus, as the equation does not account for the porosity. Although higher than experimental modulus values, Eq. 2, incorporating the porosity term, estimates reasonably good modulus values. Finally, the modulus calculated using Nielsen's relationship is in good agreement with experimental values. The small discrepancies between calculated and experimental modulus values could be attributed to the influence of pore geometry, neck size, stress concentrations, etc.

Based on present experimental results, it can be concluded that the properties of porous metallic biomaterials can be tailored to suit the natural human bone properties, by using different design approaches in combination with appropriate laser process parameters. LENS™ process can be used to fabricate actual implants with designed porosities and can be extended to other metallic biomaterials.

Conclusions:

Applicants herein disclose and describe that by using proposed novel design concepts coupled with solid freeform fabrication method metallic implants with three dimensionally interconnected porosities down to 70 vol % can be successfully fabricated. It is shown that the porosities and mechanical properties of laser processed CP Ti structures with interconnected porosity and/or novel internal architecture can be tailored by changing the LENS™ process parameters. Young's modulus and compressive strength of porous Ti samples having the porosity in the range of 35-42 vol % are close to those of human cortical bone.

References Cited in this Example and Incorporated Herein:
1. www.datamonitor.com
2. Kuroda D, Niinomi M, Morinaga M, Kato Y, Yashiro T., Design and mechanical properties of new β type titanium alloys for implant materials, *Mater Sci Eng A.*, 243 (1998) pp 244-249.
3. Seah K H W, Thampuran R, Teoh S H., The influence of pore morphology on corrosion, *Corrosion Sci*, 40 (1998) pp 547-556.
4. Okazaki Y, Nishimura E, Nakada H, Kobayashi K., Surface analysis of Ti-15Zr-4Nb-4Ta alloy after implantation in rat tibia, *Biomaterials,* 22 (2001) pp 599-607.
5. Parr G., Titanium: the mystery metal of implant dentistry, *J Prosthet Dent,* 54 (1985) pp 410-413.
6. Kasemo B, Lausema J. *Metal selection and surface characteristics*. In: Branemark P I, Zarb A G, Albreksson T, Editors, *Prosthesis*, Quintessence, Chicago, (1985) pp 99-116.
7. Robertson D M, Pierre L, Chahal R. Preliminary observations of bone ingrowth into porous materials. *J Biomed Mater Res,* 10 (1976) pp 335-344.
8. Cameron H U, Macnab I, Pilliar R M. A porous metal system for joint replacement surgery. *Int J Artif Organs,* 1 (1978) pp 104-109.
9. Head W C, Bauk D J, Emerson Jr R H. Titanium as the material of choice for cementless femoral components in total hip arthroplasty. *Clin Orthop. Relat Res.,* 311 (1995) pp 85-90.
10. Moyen B J, Lahey P J, Weinberg E H, Harris W H., Effects on intact femora of dogs of the application and removal of metal plates. A metabolic and structural study comparing stiffer and more flexible plates, *J Bone Joint Surg. Am,* 60A (1978) pp 940-947.
11. Uhthoff H K, Finnegan M., The effects of metal plates on post-traumatic remodelling and bone mass, *J Bone Joint Surg. Br,* 65-B (1983) pp 66-71.

12. Schneider E, Kinast C, Eulenberger J, Wyder D, Eskilsson G and Perren S M, A comparative study of the initial stability of cementless hip prostheses, *Clin Orthop. Relat Res.*, 248 (1989) pp 200-209.
13. Pillar R M. Porous-surfaced metallic implants for orthopaedic applications. *J Biomed Mater Res.—App Biomater,* 21 (Al) (1987) pp 1-33.
14. Clemow A J T, Weinstein A M, Klawitter J J, Koeneman J, Anderson J. Interface mechanics of porous titanium implants. *J Biomed Mater Res.*, 15 (1981) pp 73-82.
15. Asaoka K, Kuwayama N, Okuno O, Miura I. Mechanical properties and biomechanical compatibility of porous titanium for dental implants. *J Biomed Mater Res.*, 19 (1985) pp 699-713.
16. Young F A, Spector M, Kresch C H. Porous titanium endosseous dental implants in Rhesus monkey: Microradiography and histological evaluation. *J Biomed Mater Res.*, 13 (1979) pp 843-856.
17. Hahn H, Palich W. Preliminary evaluation of porous metal surface titanium for orthopedic implants. *J Biomed Mater Res.*, 4, (1970) pp 571-577.
18. Park J B, Lakes R S. *Biomaterials: An introduction.* 2nd Ed., Plenum, N.Y. (1992).
19. Walt M J, Lamprecht E G. Bone ingrowth into an open porous surface. *Trans 38th Orthop Res Soc.*, 360 (1992).
20. Jasty M, Bragdon C R, Haire T, Mulroy R D Jr, Harris H. Comparison of bone ingrowth into cobalt chrome sphere and titanium fiber mesh porous coated cementless canine acetabular components. *J Biomed Mater Res.*, 27 (1993) pp 639-644.
21. Fujisawa A, Noda I, Nishio Y, Okimatsu H. The development of the new titanium arc-sprayed artificial joints. *Mater Sci Eng C.*, 2 (1995) pp 151-157.
22. Bloebaum R D, Mihalopolulus N L, Jensen J W, Dorr L D. Post mortem analysis of bone growth into porous-coated acetabular components. *J Bone Joint Surg.*, 79 (1997) pp 1013-1022.
23. Cook S, Georgette F, Skinner M, Haddad R. Fatigue properties of carbon and porous Ti-6A14V alloy. *J Biomed Mater Res.*, 18 (1984) pp 497-512.
24. Yue S, Pilliar R, Weatherly G. The fatigue strength of porous coated Ti-6A14V implant alloy. *J Biomed Mater Res.*, 18 (1984) pp 1043-1058.
25. Oh I H, Nomura N, Masahashi N, Hanada S. Mechanical properties of porous titanium compacts prepared by powder sintering. *Scripta Mater.*, 49 (2003) pp 1197-1202.
26. Wen C E, Mabuchi M, Yamada Y, Shimojima K, Chino Y, Asahina T. Processing of biocompatible porous Ti and Mg, *Scripta Mater.*, 45 (2001) pp 1147-1153.
27. Garrett Ryan, Abhay Pandit, Dimitrios Panagiotis Apatsidis, Fabrication methods of porous metals for use in orthopaedic applications, *Biomaterials,* 27 (13) (2006) pp 2651-2670.
28. R. Banerjee, S. Nag, H. L. Fraser, A novel combinatorial approach to the development of beta titanium alloys for orthopaedic implants, *Materials Science and Engineering C.*, 25 (2005) pp 282-289.
29. X. D. Zhang, C. Brice, D. W. Mahaffey, H. Zhang, K. Schwendner, D. J. Evans and H. L. Fraser, Characterization of Laser-deposited TiAl alloys, *Scripta mater.*, 44 (2001) pp 2419-2424.
30. Katrin I. Schwendner, Rajarshi Banerjee, Peter C. Collins, Craig A. Brice, and Hamish L. Fraser, Direct laser deposition of alloys from elemental powder blends, *Scripta Materialia.*, 45 (2001) pp 1123-1129.
31. R. Banerjee, P. C. Collins, A. Gen, H. L. Fraser, Direct laser deposition of in situ Ti-6Al-4V-TiB composites, *Materials Science and Engineering A.*, 358 (2003) pp 343-349.
32. Weiping Liu, J. N. DuPont, Fabrication of functionally graded TiC/Ti composites by Laser Engineered Net Shaping, *Scripta Materialia.*, 48 (2003) pp 1337-1342.
33. P. C. Collins, R. Banerjee, S. Banerjee, H. L. Fraser, Laser deposition of compositionally graded titanium-vanadium and titanium-molybdenum alloys, *Materials Science and Engineering A.*, 352 (2003) pp 118-128.
34. X. Lin, T. M. Yue, H. O. Yang, W. D. Huang, Laser rapid forming of SS316L/Rene88DT graded material, *Materials Science and Engineering A.*, 391 (2005) pp 325-336.
35. R. Banerjee, P. C. Collins, D. Bhattacharyya, S. Banerjee, H. L. Fraser, Microstructural evolution in laser deposited compositionally graded α/β titanium-vanadium alloys, *Acta Materialia.*, 51 (2003) pp 3277-3292.
36. X. Wu, J. Mei, Near net shape manufacturing of components using direct laser fabrication technology, *Journal of Materials Processing Technology.*, 135 (2003) pp 266-270.
37. Gary K. Lewis, Eric Schlienger, Practical considerations and capabilities for laser assisted direct metal deposition, *Materials and Design.*, 21 (2000) pp 417-423.
38. R. Banerjee, C. A. Brice, S. Banerjee, H. L. Fraser, Microstructural evolution in laser deposited Ni-25 at. % Mo alloy, *Materials Science and Engineering A.*, 347 (2003) pp 1-4.
39. J. Dutta Majumdar, A. Pinkerton, Z. Liu, I. Manna, L. Li, Microstructure characterisation and process optimization of laser assisted rapid fabrication of 316L stainless steel, *Applied Surface Science.*, 247 (2005) pp 320-327.
40. Xinhua Wu, Jing Liang, Junfa Mei, C. Mitchell, P. S. Goodwin, W. Voice, Microstructures of laser-deposited Ti-6Al-4V, *Materials and Design.*, 25 (2004) pp 137-144.
41. Thieme M, Wieters K P, Bergner F, Scharnweber D, Worch H, Ndop J, et al. Titanium Powder Sintering for Preparation of a Porous FGM Destined as a Skeletal Replacement Implant, *Mater Sci Forum.*, 308 (1999) pp 374.
42. Mark P. Staiger, Alexis M. Pietak, Jerawala Huadmai, George Dias, Magnesium and its alloys as orthopedic biomaterials: A review, *Biomaterials.*, 27 (2006) pp 1728-1734.
43. Eudier M. *Powder Metall.*, 5 (1962) pp 278.
44. Boccaccini A R, Ondracek G, Mombello E, Determination of stress concentration factors in porous materials, *J. Mater Sci Lett.*, 15 (1995) pp 534-536.
45. Vassilis Karageorgiou, DavidKaplan, Porosity of 3D biomaterial scaffolds and osteogenesis, *Biomaterials.*, 26 (2005) pp 5474-5491.
46. Kalpana S. Katti, Biomaterials in total joint replacement, *Colloids and Surfaces B: Biointerfaces.*, 39 (2004) pp 133-142.
47. Mitsuo Niinomi, Recent metallic materials for biomedical applications, *Metallurgical and Materials Transactions.*, 33A (3) (2002) pp 477-486.
48. T. W. Clyne, P. J. Withers, An Introduction to Metal Matrix Composites, Cambridge University Press, Cambridge (1993).
49. Zimmerman, R. W., King, M. S. and Monterio, P. J. M., "The Elastic Modulus of Mortar as a Porous Granular Material", *Cement and Concrete Research,* 16 (2) (1986), pp 239-245.

50. L. F. Nielsen, "Elasticity and Damping of Porous Materials and Impregnated Materials," J. Am. Ceram. Soc., 67 [2] (1984) pp 93-98.

The invention claimed is:

1. A method of producing a porous metal or metal-based composite device, comprising:
    obtaining input data from bone imaging scans of a patient;
    selecting at least one of a density, a modulus of elasticity or a compression strength of a device for bone tissue engineering based on the obtained input data from the bone imaging scans of the patient; and
    forming the device for bone tissue engineering of a biocompatible metal or metal-based composite to have the selected at least one of the density, the modulus of elasticity, or the compression strength, wherein forming the device includes:
        focusing a laser onto a portion of a substrate;
        introducing particles of the biocompatible metal or metal-based composite into the focused laser in a laser-material interaction zone;
        controlling a laser energy density of the focused laser to only partially melt surfaces of the introduced particles in the laser-material interaction zone, thereby joining the particles together due to the presence of a liquid metal at the surfaces of the particles to create porosity between adjoining particles;
        depositing the introduced particles on the portion of the substrate and removing the focused laser from the portion of the substrate to allow the deposited particles to solidify and form a part of the device; and
        repeating the focusing, introducing, controlling, and depositing operations on additional portions of the substrate to form the device having an exterior surface, an interior voided core area, and a porous exterior surface region, and wherein a porosity vol% gradient increases from the exterior surface, through the porous exterior surface region, and toward the interior voided core area.

2. The method of claim 1, further comprising performing surface modifications to the porous exterior surface region to encourage cell growth and adhesion thereon.

3. The method of claim 1 wherein controlling the laser energy density of the focused laser further includes controlling the laser energy density of the focused laser to avoid completely melting the introduced particles.

4. The method of claim 1, further comprising varying an interaction time between the introduced particles and the focused laser according to a selected porosity corresponding to the portion of the substrate.

5. A method of producing a device for bone tissue engineering, comprising:
    fabricating, using a solid freeform fabrication technique, a member of a biocompatible metal or metal-based composite, including:
        focusing a laser onto a portion of a substrate;
        introducing particles of the biocompatible metal or metal-based composite into the focused laser in a laser-material interaction zone;
        only partially melting surfaces of the introduced particles with the focused laser in the laser-material interaction zone, thereby joining the particles together due to presence of a liquid metal at surfaces of the particles to create porosity between adjoining particles;
        depositing the introduced particles on the portion of the substrate and subsequently allowing the deposited particles to solidify to form a part of the member; and
        repeating the focusing, introducing, only partially melting, and depositing operations on additional portions of the substrate to form the member having an exterior surface, an interior voided core area of void fraction between 50% and 90% by volume, and a porous exterior surface region configured to encourage cell growth and adhesion thereon, wherein a porosity vol % gradient increases from the exterior surface, through the porous exterior surface region, and toward the interior voided core area.

6. The method of claim 5 wherein a transition of the porosity vol % gradient is continuous or seamless.

7. The method of claim 5 wherein the member comprises at least one of titanium (Ti); aluminum (Al); iron (Fe); or vanadium (V);.

8. The method of claim 5 wherein repeating the focusing, introducing, only partially melting, and depositing operations include varying a distance between two successive laser scans according to the increasing porosity vol % gradient.

9. The method of claim 5 wherein the porous exterior surface region comprises nanoscale or microscale pores ranging from about 1 nm to about 500 nm in diameter, or from about 1 nm to about 1 μm diameter.

10. The method of claim 9 wherein the porous exterior surface region comprising the nanoscale or microscale pores is positioned to be in contact with or be inserted into a bone upon implant of the device.

11. The method of claim 9 wherein the porous exterior surface region comprising the nanoscale or microscale pores is fabricated by at least one of electrochemical etching or chemical dissolution.

12. The method of claim 5 wherein the member or a portion of the porous exterior surface region thereof comprises a material composition of metal and ceramic in a continuous or seamless gradient from a position on the porous exterior surface region having a highest ceramic content, transitioning to lowest or zero ceramic content at an interior structure position composed of metal or metal-based composite.

13. The method of claim 12 wherein the ceramic comprises an inorganic salt.

14. The method of claim 13 wherein the inorganic salt comprises at least one of calcium phosphate or calcium carbonate.

15. The method of claim 5 wherein the porous exterior surface region comprises nanoscale or microscale pores ranging from 1 nm to 500 nm in diameter, or from 1 nm to 1 μm.

16. The method of claim 5, further comprising a chemical or biological agent deposited in or on the member or in one or more pores thereof to operatively provide for release or controlled release of the agent within a recipient.

17. A method of producing a device for bone tissue engineering having a member of a biocompatible metal or metal-based composite, comprising:
    focusing a laser onto a portion of a substrate;
    introducing particles of the biocompatible metal or metal-based composite into the focused laser in a laser-material interaction zone, wherein the focused laser having laser energy density in the laser-material interaction zone such that the focused laser only partially melts surfaces of the introduced particles without completely melting the introduced particles, thereby joining the introduced particles together due to presence of a liquid metal at surfaces of the particles to create porosity between adjoining particles;

depositing the introduced particles on the portion of the substrate and subsequently allowing the deposited particles to solidify to form a part of the member; and repeating the focusing, introducing, and depositing operations on additional portions of the substrate to form additional parts of the member according to a selected porosity profile having an exterior surface, an interior voided core area of void fraction between 50% and 90% by volume, and a porous exterior surface region, wherein a porosity vol% gradient increases from the exterior surface, through the porous exterior surface region, and toward the interior voided core area.

18. The method of claim 17, further comprising:

adjusting a distance between two successive laser scans according to the selected porosity profile.

19. The method of claim 17 wherein:

repeating the focusing, introducing, and depositing operations on additional portions of the substrate to form the additional parts of the member includes repeating the focusing, introducing, and depositing operations on the additional portions of the substrate to form the additional parts of the member arranged in layers; and the method further includes adjusting a deposition angle between successive layers according to the selected porosity profile to achieve a selected orientation between pores of the successive layers, thereby forming a three-dimensionally interconnected porosity in the formed member.

20. The method of claim 17, further comprising adjusting an interaction time between the introduced particles and the focused laser according to the selected porosity profile, thereby creating a selected porosity between the adjoining particles.

* * * * *